US012089890B2

(12) United States Patent
Christian et al.

(10) Patent No.: US 12,089,890 B2
(45) Date of Patent: Sep. 17, 2024

(54) MULTI-RATE FLUID FLOW AND VARIABLE POWER DELIVERY FOR ABLATION ELECTRODE ASSEMBLIES USED IN CATHETER ABLATION PROCEDURES

(71) Applicant: St. Jude Medical, Atrial Fibrillation Division, Inc., St. Paul, MN (US)

(72) Inventors: Steven C. Christian, New Brighton, MN (US); Theodore A. Johnson, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 386 days.

(21) Appl. No.: 17/193,859

(22) Filed: Mar. 5, 2021

(65) Prior Publication Data

US 2021/0212757 A1 Jul. 15, 2021

Related U.S. Application Data

(60) Division of application No. 15/860,503, filed on Jan. 2, 2018, now Pat. No. 10,973,571, which is a
(Continued)

(51) Int. Cl.
*A61B 18/12* (2006.01)
*A61B 18/14* (2006.01)
(Continued)

(52) U.S. Cl.
CPC .............. *A61B 18/1492* (2013.01); *A61B 2018/00029* (2013.01); *A61B 2018/00357* (2013.01);
(Continued)

(58) Field of Classification Search
CPC .......... A61B 18/1492; A61B 2218/002; A61B 2018/00648; A61B 2018/00702;
(Continued)

(56) References Cited

U.S. PATENT DOCUMENTS 5,290,263 A   3/1994   Wigness et al.
5,348,554 A   9/1994   Imran et al.
(Continued)

FOREIGN PATENT DOCUMENTS

EP        2204132 A1     7/2010
JP     2010-505596 A     2/2010
(Continued)

OTHER PUBLICATIONS

International Search Report and Written Opinion of ISA for PCT/US2012/023355 mailed Jun. 4, 2012.
(Continued)

*Primary Examiner* — Thomas A Giuliani
(74) *Attorney, Agent, or Firm* — Armstrong Teasdale LLP

(57) ABSTRACT

A system for providing irrigation fluid during ablation of tissue includes a catheter, an electrode assembly, at least one thermal sensor adapted to be connected to the catheter, and a control system. The electrode assembly is adapted to be connected to an ablation generator. The thermal sensor is adapted to be operatively connected to an electronic control unit (ECU). The ECU receives as an input temperature measurement data from the thermal sensor; determines a power delivery rate value for the ablation generator responsive to the temperature measurement data; and outputs the power delivery rate value. The control system also delivers irrigation fluid to the irrigated catheter at a first flow rate in a first time period and at a second flow rate in a second time period that is temporally after the first time period. The second flow rate is at least half of the first flow rate.

19 Claims, 18 Drawing Sheets

Related U.S. Application Data continuation of application No. 13/151,750, filed on Jun. 2, 2011, now Pat. No. 9,855,094, which is a continuation-in-part of application No. 12/979,803, filed on Dec. 28, 2010, now Pat. No. 9,788,891.

(51) Int. Cl.

| A61B 18/00 | (2006.01) |
|---|---|
| A61B 18/02 | (2006.01) |
| A61B 18/06 | (2006.01) |
| A61B 18/08 | (2006.01) |
| A61B 18/18 | (2006.01) |
| A61B 18/24 | (2006.01) |
| A61B 34/20 | (2016.01) |

(52) U.S. Cl.
CPC ........... *A61B 2018/00648* (2013.01); *A61B 2018/00702* (2013.01); *A61B 2018/00744* (2013.01); *A61B 2018/00761* (2013.01); *A61B 2018/00791* (2013.01); *A61B 2018/00863* (2013.01); *A61B 2018/0212* (2013.01); *A61B 18/06* (2013.01); *A61B 18/082* (2013.01); *A61B 2018/1861* (2013.01); *A61B 18/24* (2013.01); *A61B 2034/2053* (2016.02); *A61B 2218/002* (2013.01); *F04C 2270/041* (2013.01)

(58) Field of Classification Search
CPC ........... A61B 2018/00029; A61B 2018/00357; A61B 2018/00005; A61B 2018/00011; A61B 2018/00744; A61B 2018/00761; A61B 2018/00791; A61B 2018/00863; A61B 2018/0212; F04C 2270/041
USPC ........ 606/32, 34, 37, 42, 45, 49; 607/96, 98, 607/99, 101, 102, 104, 113, 115, 116
See application file for complete search history.

(56) References Cited

U.S. PATENT DOCUMENTS

| 5,688,267 | A | 11/1997 | Panescu et al. |
|---|---|---|---|
| 5,735,846 | A | 4/1998 | Panescu et al. |
| 5,792,140 | A | 8/1998 | Tu et al. |
| 5,897,552 | A | 4/1999 | Edwards et al. |
| 5,902,328 | A | 5/1999 | Lafontaine et al. |
| 6,010,500 | A | 1/2000 | Sherman et al. |
| 6,017,338 | A | 1/2000 | Brucker et al. |
| 6,050,993 | A * | 4/2000 | Tu ................. A61B 18/1485 606/41 |
| 6,068,653 | A | 5/2000 | LaFontaine |
| 6,217,576 | B1 * | 4/2001 | Tu ................. A61B 18/1492 606/41 |
| 6,233,476 | B1 | 5/2001 | Strommer et al. |
| 6,328,735 | B1 | 12/2001 | Curley et al. |
| 6,464,700 | B1 | 10/2002 | Koblish et al. |
| 6,498,944 | B1 | 12/2002 | Ben-Haim et al. |
| 6,506,189 | B1 | 1/2003 | Rittman et al. |
| 6,514,251 | B1 | 2/2003 | Ni et al. |
| 6,522,930 | B1 | 2/2003 | Schaer et al. |
| 6,575,969 | B1 | 6/2003 | Rittman et al. |
| 6,579,288 | B1 | 6/2003 | Swanson et al. |
| 6,616,655 | B1 | 9/2003 | Falwell et al. |
| 6,690,963 | B2 | 2/2004 | Ben-Haim et al. |
| 6,788,967 | B2 | 9/2004 | Ben-Haim et al. |
| 6,936,047 | B2 | 8/2005 | Nasab et al. |
| 7,197,354 | B2 | 3/2007 | Sobe |
| 7,263,397 | B2 | 8/2007 | Hauck et al. |
| RE39,863 | E | 10/2007 | Smith |
| 7,344,533 | B2 * | 3/2008 | Pearson ............ A61B 18/1477 606/41 |
| 7,386,339 | B2 | 6/2008 | Strommer et al. |
| 7,389,148 | B1 | 6/2008 | Morgan |
| 7,536,218 | B2 | 5/2009 | Govari et al. |
| 7,591,816 | B2 | 9/2009 | Wang et al. |
| 7,776,034 | B2 | 8/2010 | Kampa |
| 7,815,635 | B2 | 10/2010 | Wittkampf et al. |
| 7,824,406 | B2 | 11/2010 | Wang et al. |
| 7,826,905 | B2 | 11/2010 | Chitre et al. |
| 8,273,082 | B2 | 9/2012 | Wang et al. |
| 2002/0123749 | A1 | 9/2002 | Jain |
| 2002/0169445 | A1 * | 11/2002 | Jain ................. A61B 18/1492 606/41 |
| 2003/0004506 | A1 | 1/2003 | Messing |
| 2003/0060822 | A1 | 3/2003 | Schaer et al. |
| 2003/0195510 | A1 | 10/2003 | Schaer |
| 2004/0210283 | A1 | 10/2004 | Rose et al. |
| 2004/0215183 | A1 | 10/2004 | Hoey et al. |
| 2005/0055019 | A1 | 3/2005 | Skarda |
| 2005/0090816 | A1 | 4/2005 | McClurken et al. |
| 2006/0122593 | A1 | 6/2006 | Jun |
| 2006/0287650 | A1 | 12/2006 | Cao et al. |
| 2007/0043349 | A1 | 2/2007 | Swanson et al. |
| 2007/0049915 | A1 | 3/2007 | Haemmerich et al. |
| 2007/0270791 | A1 | 11/2007 | Wang et al. |
| 2008/0065062 | A1 | 3/2008 | Leung et al. |
| 2008/0071267 | A1 | 3/2008 | Wang et al. |
| 2008/0091193 | A1 | 4/2008 | Kauphusman et al. |
| 2008/0147060 | A1 | 6/2008 | Choi |
| 2008/0161795 | A1 | 7/2008 | Wang et al. |
| 2008/0167646 | A1 | 7/2008 | Godara et al. |
| 2008/0294158 | A1 | 11/2008 | Pappone et al. |
| 2009/0093811 | A1 | 4/2009 | Koblish et al. |
| 2009/0125016 | A1 | 5/2009 | Wang et al. |
| 2009/0125017 | A1 | 5/2009 | Wang et al. |
| 2009/0163911 | A1 | 6/2009 | Cao et al. |
| 2009/0163913 | A1 | 6/2009 | Wang et al. |
| 2009/0171187 | A1 | 7/2009 | Gerhart et al. |
| 2009/0171188 | A1 | 7/2009 | Paul et al. |
| 2009/0177193 | A1 | 7/2009 | Wang et al. |
| 2009/0240248 | A1 | 9/2009 | Deford et al. |
| 2009/0240249 | A1 | 9/2009 | Chan et al. |
| 2009/0312756 | A1 | 12/2009 | Schlesinger et al. |
| 2010/0057072 | A1 | 3/2010 | Roman et al. |
| 2010/0069921 | A1 | 3/2010 | Miller et al. |
| 2010/0137859 | A1 | 6/2010 | Wang |
| 2010/0152724 | A1 * | 6/2010 | Marion ............... A61B 18/1233 606/41 |
| 2010/0152727 | A1 | 6/2010 | Gibson |
| 2010/0152731 | A1 | 6/2010 | de la Rama et al. |
| 2010/0168729 | A1 | 7/2010 | Wang et al. |
| 2010/0168736 | A1 * | 7/2010 | Wang ................. A61B 18/1492 606/41 |
| 2010/0174177 | A1 | 7/2010 | Wu |
| 2010/0211070 | A1 * | 8/2010 | Subramaniam .... A61B 18/1206 606/49 |
| 2010/0286684 | A1 | 11/2010 | Hata et al. |
| 2011/0092969 | A1 | 4/2011 | Wang et al. |
| 2011/0118724 | A1 | 5/2011 | Turner et al. |
| 2011/0264089 | A1 | 10/2011 | Zirkle et al. |
| 2011/0282342 | A1 | 11/2011 | Giovanni et al. |
| 2012/0035605 | A1 | 2/2012 | Tegg et al. |
| 2012/0165809 | A1 | 6/2012 | Christian et al. |

FOREIGN PATENT DOCUMENTS

| WO | 03/024349 A1 | 3/2003 |
|---|---|---|
| WO | 2008/045925 A2 | 4/2008 |
| WO | 2008082988 | 10/2008 |
| WO | 2008083000 | 10/2008 |
| WO | 2008083003 | 10/2008 |
| WO | 2009082574 | 2/2009 |
| WO | 2009070446 | 4/2009 |
| WO | 2012/091793 A1 | 7/2012 |

OTHER PUBLICATIONS

International Search Report and Written Opinion of ISA for PCT/US2012/026759 mailed Jul. 5, 2012.

(56) References Cited

OTHER PUBLICATIONS

International Search Report and Written Opinion of ISA for PCT/US2011/059111 mailed Apr. 13, 2012.

* cited by examiner

MULTI-RATE FLUID FLOW AND VARIABLE POWER DELIVERY FOR ABLATION ELECTRODE ASSEMBLIES USED IN CATHETER ABLATION PROCEDURES

CROSS-REFERENCE TO RELATED APPLICATIONS

This application is a continuation-in-part of U.S. patent application Ser. No. 12/979,803 entitled "Ablation Electrode Assemblies and Methods for Using Same," filed Dec. 28, 2010, now U.S. Pat. No. 9,788,891, the entire content of which is incorporated by reference herein.

BACKGROUND OF THE INVENTION a. Field of the Invention

The instant disclosure relates generally to systems and methods for providing irrigation fluid during cardiac ablation of cardiac tissue. In particular, the instant disclosure relates to families of systems and methods for providing irrigation fluid during cardiac ablation of cardiac tissue in which irrigation fluid is delivered at a first flow rate in a first time period and at a second flow rate in a second time period. The second time period is temporally after the first time period, and the second flow rate is at least half of the first flow rate. The instant disclosure also relates to systems for controlling delivery of power during cardiac ablation of cardiac tissue. In particular, the instant disclosure relates to systems in which energy is delivered at a first power level in a first time period and at a second power level in a second time period. The second time period follows the first time period, and the second power level has a magnitude of at least about (or approximately) one third (~⅓) of the first power level.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include, for example, radio frequency (RF) ablation, cryoablation, laser ablation, chemical ablation, high-intensity focused ultrasound (HIFU)-based ablation, microwave ablation. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

During RF ablation, local temperature elevation can result in coagulum formation on the ablation electrode, resulting in an impedance rise. As the impedance increases, more energy is passed through the portion of the electrode without coagulation, creating even higher local temperatures and further increasing coagulum formation and the impedance. Finally, enough blood coagulates onto the electrode that no energy passes into the targeted tissue, thereby requiring the catheter to be removed from the vascular system, the electrode to be cleaned, and the catheter to be repositioned within the cardiac system at the desired location. Not only can this process be time consuming, but it can be difficult to return to the previous location because of the reduced electrical activity in the targeted tissue, which has been previously ablated. Recent studies have also demonstrated the formation of a so-called soft thrombus in RF ablation. The formation of the soft thrombus results from heat induced protein denaturation and aggregation and occurs independently of heparin concentration in serum. In addition, RF ablation can generate significant heat, which, if not controlled, can result in excessive tissue damage, such as tissue charring, steam pop, and the like.

Accordingly, it can be desirable to monitor and/or control the temperature of ablation electrode assemblies. It can also be desirable to use ablation electrode assemblies to provide irrigation fluid during RF ablation. RF ablation catheters can be configured to provide temperature feedback during RF ablation via a thermal sensor such as a thermocouple or thermistor. A temperature reading provided by a single thermal sensor cannot accurately represent the temperature of the electrode/tissue interface. This is because a portion of the electrode that is in direct contact with the targeted tissue can have a higher temperature than the rest of the electrode that is being cooled by the blood flow. The orientation of the RF ablation catheter can affect the position of the thermal sensor, and accordingly, can affect the temperature reading provided by the thermal sensor. If the thermal sensor is in contact with the targeted tissue, the thermal sensor can provide a certain temperature reading generally corresponding to the temperature of the targeted tissue, but if the thermal sensor is not in contact with the targeted tissue, there will be a time lag before the thermal sensor provides a temperature reading generally corresponding to the temperature of the targeted tissue, and due to the cooling effect of the blood flow, the thermal sensor can never approach the actual temperature of the targeted tissue. In an effort to overcome the effect that the orientation of the catheter can have on temperature sensing, multiple thermal sensors positioned at different locations on the electrode can be used. For example and without limitation, the highest measured temperature can be used to represent the electrode/tissue interface temperature. However, temperature measurements provided by multiple thermal sensors cannot always accurately reflect the temperature of the electrode/tissue interface (e.g., heat transfer between the multiple thermal sensors can affect the temperature reading of each thermal sensor).

Accurate, real-time correlation between the temperature recorded at the distal end portion of ablation electrode assemblies and that of the targeted tissue typically becomes more difficult over time. This is because the temperature recorded at the distal end portion of ablation electrode assemblies generally plateaus, whereas the temperature of the targeted tissue continues to steadily rise over time. RF ablation would benefit from an improved correlation between the temperatures of ablation electrode assemblies and targeted tissue, especially toward the end of an RF ablation cycle. RF ablation would also benefit from a cycle configured to increase the total energy delivered during an RF ablation cycle (thereby increasing lesion size), while still sufficiently controlling temperature to avoid adverse effects such as tissue charring.

BRIEF SUMMARY OF THE INVENTION

It is desirable to be able to provide ablation electrode assemblies that are configured to mitigate the effects of orientation of the RF ablation catheter for monitoring the temperature of the ablation electrode assemblies and/or targeted tissue, as well as to mitigate temperature gradients (or the directions and rates at which temperature changes) across electrodes. It is also desirable to interrupt and/or reduce heat transfer paths between multiple thermal sensors of the electrode, thereby improving the ability to distinguish between the temperature reading associated with a thermal sensor that is proximate the lesion formed in the targeted tissue and the temperature reading associated with a thermal sensor that is proximate the circulating blood pool. It is also desirable to have improved temperature correlation between the electrode and tissue interface.

It is also desirable, in some embodiments, to segment the ablation electrode and have an independent thermal sensor associated with each segment of the ablation electrode in order to offer even more complete segregation of the individual thermal sensors.

It is also desirable, in some embodiments, to include a mechanism to irrigate the ablation electrode assemblies and/or targeted areas in a patient's body with biocompatible fluids, such as saline solution, in order to reduce charring and inhibit the formation of coagulum and/or soft thrombus, as well as to enable deeper and/or greater volume lesions as compared to conventional, non-irrigated catheters at identical power settings. This can, in turn, enable greater energy delivery during RF ablation. The flow of irrigation fluids can be turbulent in order to provide an enveloping flow pattern adjacent to the surface of the ablation electrode assemblies for mixing with, displacing, and/or diluting blood that can be in contact with the ablation electrode assemblies in order to prevent stasis and the formation of coagulum. Pulsatile flow of irrigation fluids can help prevent stagnation areas at the distal end of an electrode by increasing flow turbulence around the catheter. Pulsatile flow of irrigation fluids can also improve correlation between the temperature of the ablation electrode and the targeted tissue. In particular, certain sequences of pulsatile flow can significantly improve correlation between the temperature of the ablation electrode and the targeted tissues at or near the end of an RF ablation cycle. The flow of irrigation fluids can be modified based on information and feedback received during RF ablation. Ablation electrodes can be disposed on the distal end portion or elsewhere on an ablation catheter whether linear, coiled, or balloon-based.

It is also desirable, in some embodiments, to monitor a change in the temperature of irrigation fluids during RF ablation in order to provide additional information or feedback regarding energy delivery and/or the temperature of the electrode and tissue interface. RF ablation can be modified based on the information and feedback regarding energy delivery and/or the temperature of the electrode and tissue interface. Operation in a temperature control mode can be at a set point above 55 degrees Celsius.

The instant disclosure relates to a system for providing irrigation fluid during cardiac ablation of targeted tissue. The system comprises: a catheter shaft having a fluid lumen; an electrode assembly adapted to be connected to the catheter shaft and adapted to be electrically connected to an ablation generator that is configured to deliver energy to the electrode assembly; and at least one thermal sensor adapted to be disposed within the irrigated catheter and adapted to be operatively connected to an electronic control unit (ECU) that is also operatively connected to a source of irrigation fluid and the ablation generator. The ECU is configured to receive as an input temperature measurement data from the at least one thermal sensor; determine a power delivery rate value for the ablation generator responsive to the temperature measurement data; and output the power delivery rate value. The system further comprises a control system configured to control the delivery of irrigation fluid from the source of irrigation fluid to the irrigated catheter. The control system delivers irrigation fluid to the irrigated catheter at a first flow rate in a first time period and at a second flow rate in a second time period. The second time period is temporally after the first time period. The second flow rate is at least half of the first flow rate. The control system is further configured to receive the power delivery rate value and to control energy delivery of the ablation generator based at least in part on the power delivery rate value.

The first time period is between about 10 seconds and about 15 seconds in an embodiment of the disclosure. The ablation generator can be configured to deliver increased power during the first time period as compared to the second time period. At least one of the first flow rate and the second flow rate can be based at least in part on electrophysiological (EP) data, physiologic data, or other data obtained during cardiac ablation. The EP data, physiologic data, or other data can comprise the temperature of a tip of the irrigated catheter, the temperature of targeted tissue undergoing cardiac ablation, the electrical impedance of targeted tissue undergoing cardiac ablation, or a combination thereof. The first time period substantially coincides with the beginning of an ablation cycle in an embodiment of the disclosure.

The instant disclosure also relates to a method of delivering fluid to an irrigated catheter for cardiac ablation. The method comprises: delivering irrigation fluid within at least a portion of the irrigated catheter for a first time period, wherein the irrigation fluid has a first flow rate in the first time period; and delivering irrigation fluid within at least a portion of the irrigated catheter for a second time period, wherein the irrigation fluid has a second flow rate in the second time period. The second time period is temporally after the first time period, and the second flow rate is at least about half of the first flow rate.

The first time period can be between about 10 seconds and about 15 seconds in an embodiment of the disclosure. An ablation generator can be electrically connected to at least a portion of the irrigated catheter. The ablation generator can be configured to deliver increased power during the first time period as compared to the second time period. At least one thermal sensor can be disposed within the irrigated catheter in accordance with an embodiment of the disclosure. The ablation generator can be configured to deliver power based at least in part on temperature data obtained from the thermal sensor. At least one of the first flow rate and the second flow rate can be based at least in part on EP data, physiologic data, or other data obtained during cardiac ablation in accordance with an embodiment of the disclosure. The data can comprise the temperature of a tip of the irrigated catheter, the temperature of targeted tissue undergoing cardiac ablation, the electrical impedance of targeted tissue undergoing cardiac ablation, or a combination thereof. The first time period substantially coincides with the beginning of an ablation cycle in accordance with an embodiment of the disclosure.

The instant disclosure also relates to a system for delivering power during cardiac ablation of targeted tissue. The system comprises a catheter, an ablation generator, and a control system. The ablation generator is electrically connected to at least a portion of the catheter and is configured to deliver energy to at least the portion of the catheter. The control system is configured to control energy delivery of the ablation generator. The control system delivers energy at a first power level in a first time period and at a second power level in a second time period. The second time period is temporally after the first time period, and the second power level has a magnitude of at least about one third of the first power level.

The first time period can be between about 10 seconds and about 15 seconds in an embodiment of the disclosure. The first power level can comprise between approximately 30 Watts to 40 Watts. The second power level can comprise between approximately 10 Watts to 15 Watts. The ablation generator is configured to deliver energy at a constant power level during the first time period in accordance with an embodiment of the disclosure. The ablation generator is configured to deliver energy during the second time period based at least in part on a temperature of a tip of the catheter or a temperature of the targeted tissue, or a combination thereof. The system further includes a source of irrigation fluid in accordance with an embodiment of the disclosure. In this embodiment, the control system can be configured to deliver irrigation fluid to the catheter at a first flow rate in the first time period and at a second flow rate in the second time period. The first flow rate can be at least twice the second flow rate.

DETAILED DESCRIPTION OF THE DISCLOSURE

The instant disclosure generally relates to irrigated ablation electrode assemblies. For purposes of this description, similar aspects among the various embodiments described herein will be referred to by similar reference numbers. As will be appreciated, however, the structure of the various aspects can be different among the various embodiments.

Figure 1:
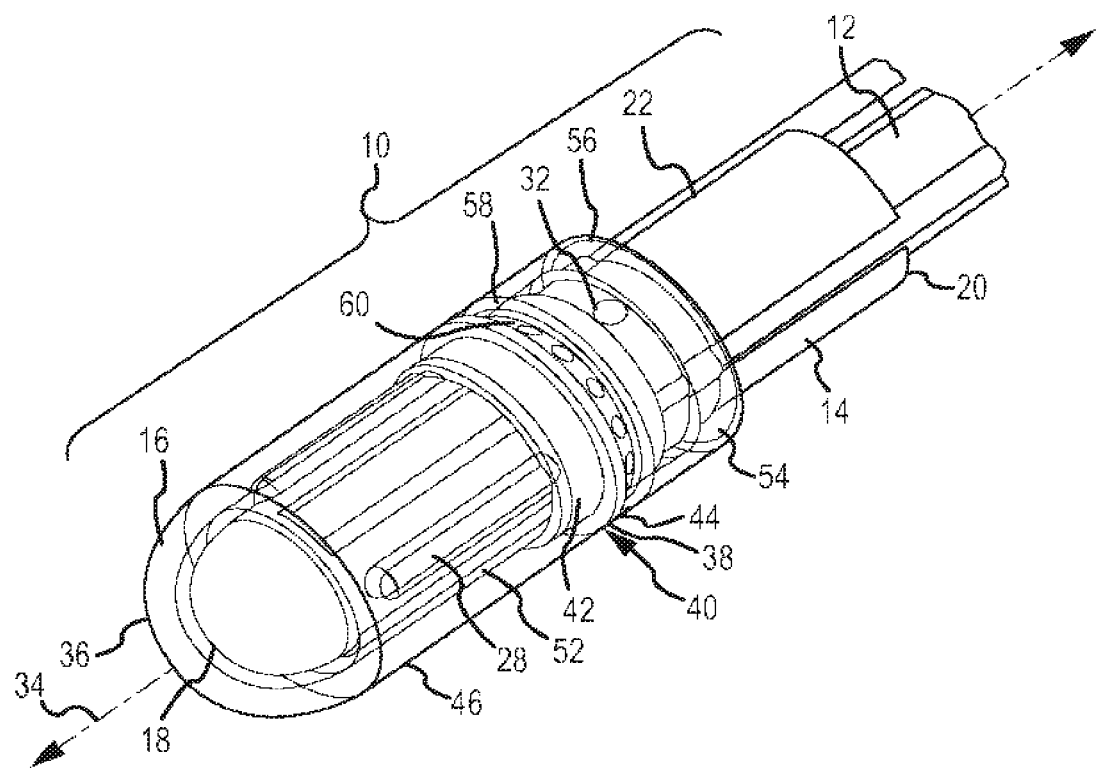
FIG. 1 is an isometric partially transparent view of an ablation electrode assembly in accordance with a first embodiment of the disclosure.
Figure 2:
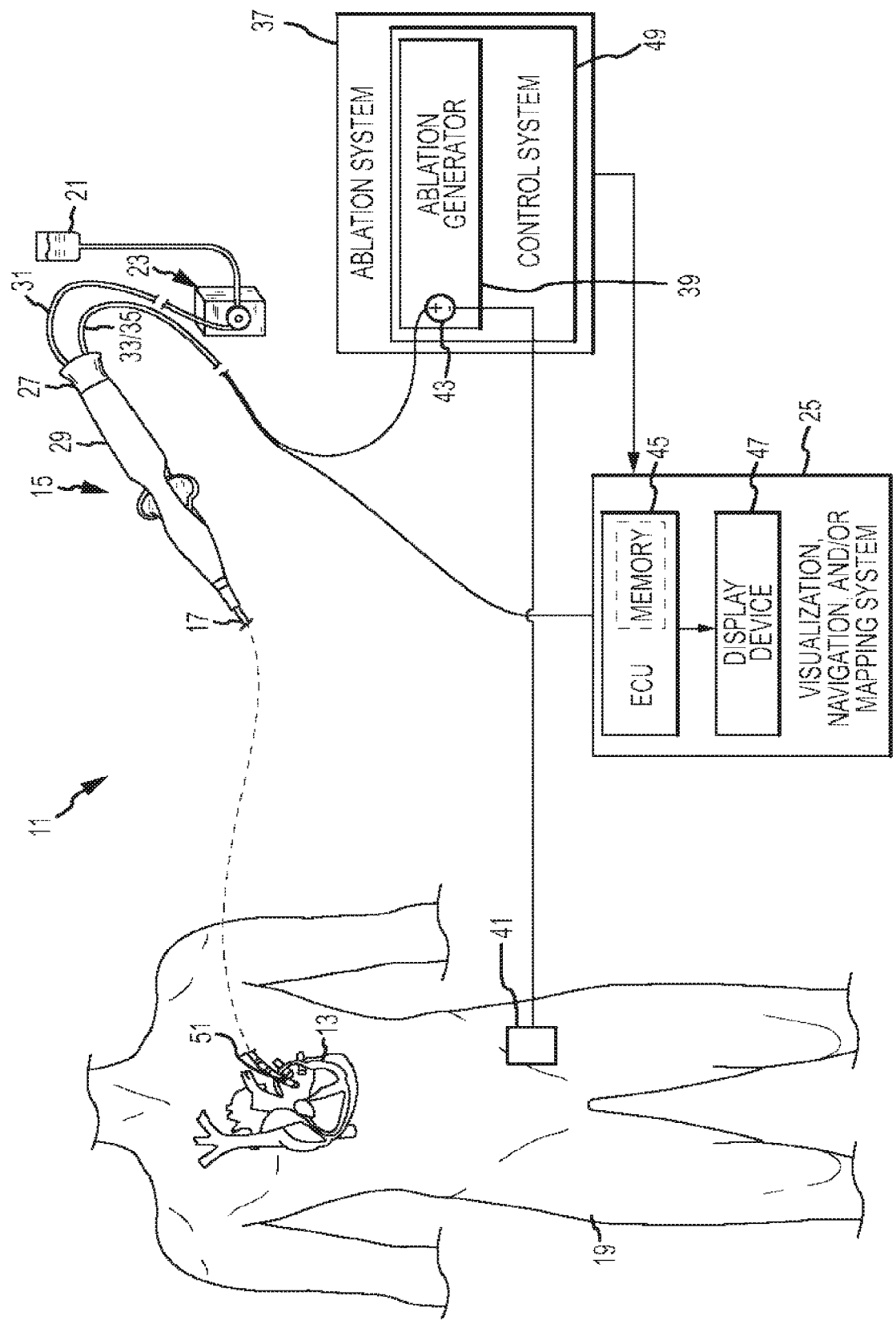
FIG. 2 is a diagrammatic view of a system for performing one more diagnostic and/or therapeutic functions in association with cardiac tissue.

An embodiment of an ablation electrode assembly 10 is generally shown in FIG. 1. Referring now to FIG. 2, the ablation electrode assembly 10 can comprise part of an irrigated catheter system 11 for examination, diagnosis, and/or treatment of internal body tissues (e.g., targeted tissue areas 13). In an exemplary embodiment, the irrigated catheter assembly can comprise an ablation catheter 15. The instant disclosure generally refers to ablation electrodes and electrode assemblies configured to deliver RF energy, but it is contemplated that the instant disclosure is equally applicable to any number of other ablation electrodes and electrode assemblies for catheters that deliver any number of other diverse types of energy where the temperature of the device and of the targeted tissue areas can be factors during diagnostic and/or therapeutic medical procedures. For example and without limitation, other ablation electrodes and electrode assemblies can deliver radio frequency (RF)

energy, cryoablation energy, ultrasound energy, HIFU energy, microwave energy, optical energy, chemical energy, or other energy.

Still referring to FIG. 2, the irrigated catheter assembly includes a catheter shaft 17 that is an elongate, tubular, flexible member configured for movement within a body. The catheter shaft 17 can be introduced into a blood vessel or other structure within a body 19 through a conventional introducer. The catheter shaft 17 can be steered or guided through a body to a desired location such as targeted tissue areas 13 with pullwires, tension elements, so-called push elements, or other means known in the art.

The irrigated catheter assembly further includes at least one fluid lumen or fluid delivery tube 12 disposed within the catheter shaft 17. The fluid delivery tube 12 is configured to supply fluid to the ablation electrode assembly 10. The fluid delivery tube 12 of the irrigated catheter assembly can be connected to a fluid source 21 providing a biocompatible fluid such as saline, or a medicament, through a pump 23, which can comprise, for example, a fixed rate roller pump or variable volume syringe pump with a gravity feed supply from the fluid source for irrigation. The fluid source 21 and/or pump 23 is conventional in the art. The fluid source 21 and/or pump 23 can comprise a commercially available unit sold under the name Cool Point™, available from St. Jude Medical, Inc. in an embodiment.

The irrigated catheter assembly can further include one or more positioning electrodes 51 mounted in or on the catheter shaft 17. The electrodes 51 can comprise, for example, ring electrodes. The electrodes 51 can be used, for example, with a visualization, navigation, and mapping system 25. The electrodes 51 can be configured to provide a signal indicative of both a position and orientation of at least a portion of the catheter shaft 17. The visualization, navigation, and/or mapping system 25 with which the electrodes 51 can be used can comprise an electric field-based system, or sometimes referred to as an impedance-based system, such as, for example, that having the model name ENSITE NAVX® (aka ENSITE® Classic as well as newer versions of the ENSITE® system, denoted as ENSITE VELOCITY™) and commercially available from St. Jude Medical, Inc. and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the electrodes 51 can be configured to be responsive to an electric field transmitted within the body 19 of the patient. The electrodes 51 can be used to sense an impedance at a particular location and transmit a representative signal to an external computer or processor. In other exemplary embodiments, however, the visualization, navigation, and/or mapping system 25 can comprise other types of systems, such as, for example and without limitation: a magnetic field- and current-based system such as the CARTO 3™ System (with current- and magnetically-driven or receptive electrodes) available from Biosense Webster, and as generally shown with reference to one or more of U.S. Pat. No. 6,498,944 entitled "Intrabody Measurement," 6,788,967 entitled "Medical Diagnosis, Treatment and Imaging Systems," and 6,690,963 entitled "System and Method for Determining the Location and Orientation of an Invasive Medical Instrument," the entire disclosures of which are incorporated herein by reference, or the gMPS® system from MediGuide Ltd. of Haifa, Israel (now owned by St. Jude Medical, Inc.), and as generally shown with reference to one or more of U.S. Pat. No. 6,233,476 entitled "Medical Positioning System," 7,197,354 entitled "System for Determining the Position and Orientation of a Catheter," and 7,386,339 entitled "Medical Imaging and Navigation System," the entire disclosures of which are incorporated herein by reference. In accordance with a magnetic field-based system, the catheter can be configured to include field sensors (e.g., coils) responsive to a magnetic field transmitted through the body 19 of the patient to sense the strength of the field at a particular location and transmit a representative signal to an external computer or processor. Such field sensors can comprise one or more metallic coils located on or within the catheter shaft 17 in a magnetic field-based system. As noted above, a combination electric field-based and magnetic field-based system such as the CARTO 3™ System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the catheter can include both electrodes 51 as one or more impedance-based electrodes and one or more magnetic field-sensing coils. Commonly available fluoroscopic, computed tomography (CT), and magnetic resonance imaging (MRI)-based systems can also be used.

The irrigated catheter assembly can include other conventional components such as, for example and without limitation, conductors associated with the electrodes, and possibly additional electronics used for signal processing, visualization, localization, and/or conditioning. The irrigated catheter assembly can further include multiple lumens for receiving additional components. The irrigated catheter assembly can further include a cable connector or interface 27 and a handle 29. The cable connector or interface 27 can provide mechanical, fluid, and electrical connection(s) for cables 31, 33, 35 extending from the pump 23 and/or an ablation system 37 as described in more detail below. The cable connector or interface 27 can be conventional in the art and can be disposed at the proximal end of the irrigated catheter assembly. The handle 29 can provide a location for the clinician to hold the irrigated catheter assembly and can further provide means for steering or guiding the catheter shaft 17 within the body 19 as known in the art. Catheter handles are generally conventional in the art and it will be understood that the construction of the handle can vary. In an embodiment, for the purpose of steering the catheter shaft 17 within the body 19, the handle 29 can be substituted by a controllable robotic actuator.

Figure 3:
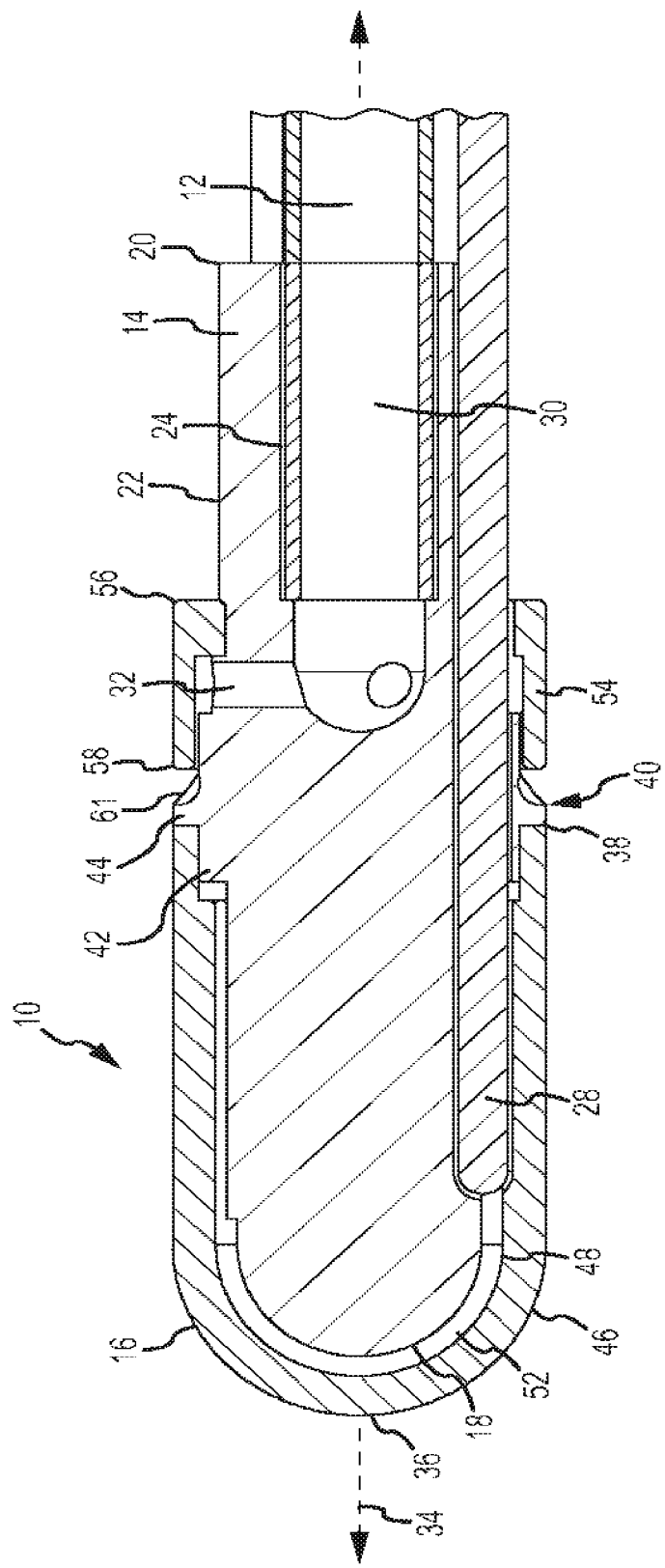
FIG. 3 is a cross-sectional view of the ablation electrode assembly of FIG. 1.

Ablation electrode assembly 10 can be connected to and/or coupled with the catheter shaft 17. Ablation electrode assembly 10 can be disposed at or near the distal end of the catheter shaft 17. Ablation electrode assembly 10 can be disposed at the extreme distal end (e.g., tip) of the catheter shaft 17. Referring now to FIGS. 1 and 3, the ablation electrode assembly 10 can include an inner core member 14 and an outer shell 16 in accordance with a first embodiment of the disclosure. The lengths and/or diameters of inner core member 14, outer shell 16, ablation electrode assembly 10, as well as portions thereof, can vary depending on the design of ablation electrode assembly 10. The outer shell 16 can be about 4 millimeters in length in an embodiment.

Inner core member 14 is provided to interrupt and/or reduce the heat transfer path through the ablation electrode assembly 10 and provide an insulated internal flow path for irrigation fluid. More particularly, inner core member 14 can be provided to interrupt and/or reduce the heat transfer path between multiple thermal sensors located within the ablation electrode assembly 10 as described in more detail below. By interrupting and/or reducing the heat transfer path between multiple thermal sensors located within the ablation electrode assembly 10, it can improve the ability of a catheter incorporating the ablation electrode assembly 10 to distinguish the higher temperature associated with lesion formation at the interface between the electrode of the ablation electrode assembly 10 and the targeted tissue.

Inner core member 14 comprises a thermal insulator having a reduced thermal conductivity. Inner core member 14 can be thermally nonconductive in accordance with an embodiment of the disclosure. Inner core member 14 can comprise an electrically nonconductive material in accordance with an embodiment of the disclosure. In general, the inner core member 14 is lower in thermal conductivity, and preferably substantially lower, than outer shell 16. Inner core member 14 can comprise a reduced thermally conductive polymer in accordance with an embodiment of the disclosure. A reduced thermally conductive polymer is one with physical attributes that decrease heat transfer by about 10% or more, provided that the remaining structural components are selected with the appropriate characteristics and sensitivities desired for the ablation electrode assembly 10. One reduced thermally conductive material can include polyether ether ketone (PEEK). Additional examples of thermally nonconductive or reduced thermally conductive materials that can be useful in conjunction with the instant disclosure include, but are not limited to, high density polyethylene (HDPE), polyimide thermoplastic resins, such as ULTEM® as provided by General Electric Plastics (now known as SABIC Innovative Plastics), polyaryletherketones, polyurethane, polypropylene, oriented polypropylene, polyethylene, crystallized polyethylene terephthalate, polyethylene terephthalate, polyester, polyetherimide, acetyl, ceramics, and/or various combinations thereof. Inner core member 14 can also comprise other plastic materials such as silicone or polyether block amides such as those sold under the trademark PEBAX® and generally available from Arkema France in other embodiments of the disclosure.

Figure 4:
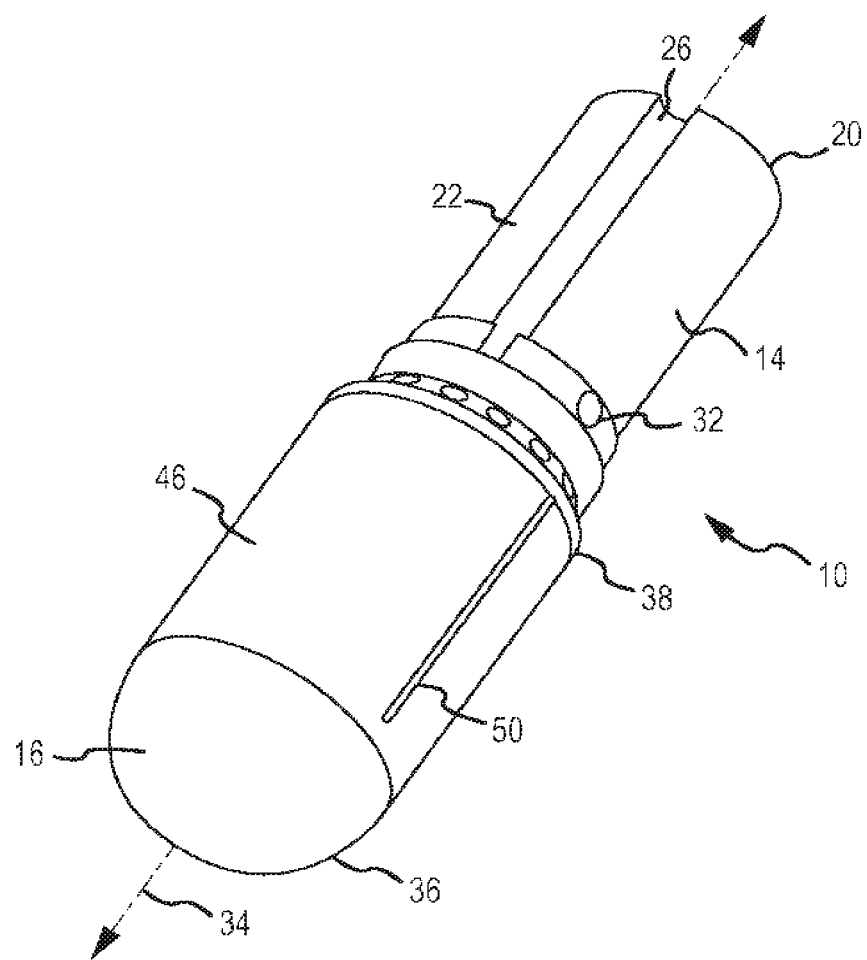
FIG. 4 is an isometric view of the ablation electrode assembly of FIG. 1.

Inner core member 14 has a distal end 18 and a proximal end 20. Inner core member 14 can be generally cylindrical in shape. The distal end 18 of the inner core member 14 can be partially spherical or generally hemispherical in shape in accordance with an embodiment of the disclosure. The proximal end 20 of the inner core member 14 can be configured for coupling and/or connecting inner core member 14 with the catheter shaft. The proximal end 20 of the inner core member 14 can also be configured to receive the fluid delivery tube 12. The inner core member 14 can include multiple lumens for receiving any number of components (e.g., wires and the like) which can be routed through the inner core member 14. As best illustrated in FIG. 3, the inner core member 14 also has an outer surface 22 and an inner surface 24. As best illustrated in FIG. 4, the outer surface 22 of the inner core member 14 includes a channel 26. The outer surface 22 of the inner core member 14 includes a plurality of channels 26 in an embodiment of the disclosure.

As best illustrated in FIGS. 1 and 3, each of the plurality of channels 26 is configured to receive a thermal sensor 28. Accordingly, the ablation electrode assembly 10 can include a plurality of thermal sensors 28 in accordance with an embodiment of the disclosure. The ablation electrode assembly 10 can include three thermal sensors 28 in accordance with an embodiment of the disclosure. The thermal sensors 28 can be substantially equally spaced around the periphery or circumference of the inner core member 14. Although three sensors that are substantially equally spaced are mentioned herein, the ablation electrode assembly 10 can include fewer or more thermal sensors 28 in other embodiments and the location of the thermal sensors 28 can vary in other embodiments. For example, in an embodiment, a single thermal sensor 28 can be centered within the ablation electrode assembly 10. Thermal sensors 28 can be connected and/or coupled to inner core member 14 (and/or ablation electrode assembly 10) in any manner that is conventional in the art to hold thermal sensors 28 in place relative to inner core member 14 (and/or ablation electrode assembly 10). Thermal sensors 28 are configured for measurement and temperature control/regulation of ablation electrode assembly 10. Thermal sensors 28 can be any mechanism known to one of ordinary skill in the art, including for example and without limitation, thermocouples and/or thermistors. Thermal sensors 28 can comprise other types of devices, such as for example and without limitation, devices for determining pressure, temperature and a flow parameter of a flowing fluid available from Radi Medical Systems AB, and as generally shown with reference to at least U.S. Pat. No. RE39,863 entitled "Combined flow, pressure and temperature sensor," the entire disclosure of which is incorporated herein by reference.

Inner surface 24 defines an inner cavity 30 as best illustrated in FIG. 3. In an embodiment of the disclosure, the inner core member 14 includes a radially extending passageway 32 that extends from the inner cavity 30 to the outer surface 22 of the inner core member 14. Inner core member 14 includes a plurality of radially extending passageways 32 in an embodiment. Each of the radially extending passageways 32 extend from the inner cavity 30 of the inner core member 14 to the outer surface 22 of the inner core member 14. Each of the radially extending passageways 32 can be substantially centrally located on the inner core member 14 relative to a longitudinal axis 34 of the ablation electrode assembly 10. In an embodiment, the radially extending passageways 32 can be oriented at about 90 degrees relative to the longitudinal axis 34 of the ablation electrode assembly 10. In accordance with other embodiments, the radially extending passageways 32 can be angled generally toward the distal end 18 of the inner core member at an acute angle (e.g., between about 20 to about 70 degrees, and for some embodiments, between about 30 to about 65 degrees) with respect to the longitudinal axis 34 of the ablation electrode assembly 10. The orientation of the radially extending passageways 32 vary depending on the design of the ablation electrode assembly 10. The radially extending passageways 32 of the inner core member 14 can be straight or curved in various embodiments of the disclosure. In accordance with an embodiment of the disclosure, the radially extending passageways 32 of the inner core member 14 can be diametrically opposed to each other around the perimeter or circumference of the inner core member 14. The radially extending passageways 32 can be generally tubular and can have a constant diameter along their length. In an embodiment, radially extending passageways 32 can have a diameter ranging in size from about 0.008 to about 0.015 inches, and for some embodiments between about 0.010 to about 0.012 inches. Alternate configurations having various shapes and diameters, for example, along all or portions of the length of the radially extending passageways 32 can be used in various embodiments. Radially extending passageways 32 can be configured to provide proximal delivery of irrigation fluid. Delivery of irrigation fluid generally reduces char, thrombus formation, and coagulum formation, thereby enabling greater energy delivery during RF ablation. Delivery of irrigation fluid can displace blood and prevent stasis in the areas adjacent the outer shell 16 of the ablation electrode assembly 10.

Outer shell 16 improves temperature correlation between the electrode and tissue interface because it is configured as a thin shell, in place of a solid mass. The thin shell design can also mitigate temperature gradients across the ablation electrode assembly 10, as well as mitigate the effects of orientation of a catheter incorporating the ablation electrode assembly 10 in connection with monitoring the temperature of the ablation electrode assembly 10 and/or targeted tissue.

Outer shell 16 can be a thin shell with a small thickness and can be external to and/or surround the inner core member 14. Outer shell 16 can comprise a single layer. Outer shell 16 can be comprised of any electrically, and potentially thermally, conductive material known to those of ordinary skill in the art for the delivery of ablative energy to targeted tissue areas. Examples of electrically conductive materials include gold, platinum, iridium, palladium, stainless steel, and/or any combination thereof. In particular, a combination of platinum and iridium can be used in various combinations. Outer shell 16 can be fabricated or constructed in accordance with any method or technique known to one of ordinary skill in the art. For example and without limitation, outer shell 16 can be fabricated or constructed using so-called deep drawn metal forming techniques, metal-punching techniques, electroforming techniques (e.g., electroforming over a sacrificial form that can include rods or other internal forms that melt or are subsequently dissolved), powdered metal techniques (e.g., pressing powered metal into a slug, sintering at high heat, and then covering the pressed and sintered slug with a metallic covering member), liquid metal injection molding (MIM) techniques, and the like. The powered metal techniques can also include sacrificial members, and the pressed and sintered slug can itself conduct fluid and thermal energy inside, around, and against the metallic covering.

Outer shell 16 can be electrically connected to an ablation system 37 to allow for the delivery of ablative energy, or the like. Outer shell 16 can be electrically connected to an ablation system 37 in any manner conventional in the art. For example, a power wire 35 (best illustrated in FIG. 7) can be provided within outer shell 16 of ablation electrode assembly 10. The power wire 35 can extend through a lumen(s) provided within the ablation electrode assembly 10. The irrigated catheter assembly can be configured for operation at an initial power setting of up to 50 Watts.

The ablation system 37 can be comprised of, for example, an ablation generator 39 one or more ablation patch electrodes 41. The ablation generator 39 generates, delivers, and controls ablation energy (e.g., RF) output by the irrigated catheter assembly and the outer shell 16 of the ablation electrode assembly 10 thereof, in particular. The generator 39 is conventional in the art and can comprise a commercially available unit sold under the model number IBI-1500T RF Cardiac Ablation Generator, available from St. Jude Medical, Inc. In an exemplary embodiment, the generator 39 can include an RF ablation signal source 43 configured to generate an ablation signal that is output across a pair of source connectors: a positive polarity connector SOURCE (+), which electrically connects to the outer shell 16 of the ablation electrode assembly 10 of the irrigated catheter assembly; and a negative polarity connector SOURCE (−), can be electrically connected to one or more of the patch electrodes 41. It should be understood that the term connectors as used herein does not imply a particular type of physical interface mechanism, but is rather broadly contemplated to represent one or more electrical nodes (including multiplexed and de-multiplexed nodes). The source is configured to generate a signal at a predetermined frequency in accordance with one or more user specified control parameters (e.g., power, time, etc.) and under the control of various feedback sensing and control circuitry. The source can generate a signal, for example, with a frequency of about 450 kHz or greater for RF energy. The generator 39 can also monitor various parameters associated with the ablation procedure including, for example, impedance, the temperature at the distal tip of the irrigated catheter assembly, applied ablation energy, power, force, proximity, and the position of the irrigated catheter assembly, and provide feedback to the clinician or another component within the irrigated catheter assembly regarding these parameters. Operation in a temperature control mode can be, for example, at a set point above 50 degrees Celsius.

Outer shell 16 has a distal end 36 and a proximal end 38. Outer shell 16 can be generally cylindrical in shape. The distal end 36 of the outer shell 16 can be partially spherical or generally hemispherical in shape in accordance with an embodiment of the disclosure. The proximal end 38 of outer shell 16 can be configured for connection to the inner core member 14. Outer shell 16 can be coupled together or connected with inner core member 14 along the same longitudinal axis 34. Inner core member 14 and outer shell 16 can be connected or coupled together by any known mechanisms including, for example and without limitation, adhesive bonding, press-fit configurations, snap-fit configurations, ultrasonic staking, mechanical deformation, or any other mechanism known to one of ordinary skill in the art. In an embodiment, a connecting member 40 can be used to connect the outer shell 16 to the inner core member 14. For example, the connecting member 40 can comprise a generally annular ring 42 and a radially outwardly extending flange 44 at an axial (e.g., proximal) end of the generally annular ring 42. The generally annular ring 42 can have an outer diameter that is substantially equal to the inner diameter of the outer shell 16 at the proximal end 38 of the outer shell 16. The radially outwardly extending flange 44 of the connecting member 40 can have an outer diameter that is substantially equal to the outer diameter of the outer shell 16. At least a portion of the outer shell and the radially outwardly extending flange 44 can be connected using any of the mechanisms for connection described above. In the embodiment described above, the connecting member 40 can be separate from the remainder of the inner core member 14, such that the inner core member 14 and connecting member 40 form a multiple-piece assembly. In other embodiments, the connecting member 40 can be integral with the inner core member 14, such that the inner core member 14 and connecting member 40 form a single-piece assembly.

The outer shell 16 also has an outer surface 46 and inner surface 48 as best illustrated in FIG. 3. As best illustrated in FIG. 4, the outer surface 46 of the outer shell 16 can be scored with at least one slot 50. The outer surface 46 of the outer shell 16 can be scored with a plurality of grooves or slots 50 in accordance with an embodiment of the disclosure. Each of the plurality of grooves or slots 50 can extend axially, parallel to the longitudinal axis 34 of the ablation electrode assembly 10. Each of the plurality of grooves or slots 50 can extend from the proximal end 38 of the outer shell 16 toward the distal end 36 of the outer shell 16. Each of the plurality of grooves or slots 50 can extend for a substantial portion of the axial length of the outer shell 16. Each of the plurality of grooves or slots 50 can be configured to separate the outer shell 16 into a plurality of segments. The ablation electrode assembly 10 can include a separate, individual thermal sensor 28 for each of the plurality of segments of the outer shell 16. By separating the outer shell 16 into a plurality of segments, more complete segregation of individual thermal sensors 28 can be obtained. In an embodiment, at least one retaining wire and/or safety wire (not shown) can be extended through a lumen in the catheter shaft and can be connected to the ablation electrode assembly 10. The retaining wire and/or safety wire can be configured to ensure that that the ablation electrode assembly 10 is not separated from the catheter shaft to which it is attached during movement of the irrigated catheter assembly within a body.

Inner core member 14 and outer shell 16 define a space 52. Space 52 can further interrupt and/or reduce the heat transfer path between multiple thermal sensors 28. The configuration of the space 52 can vary greatly and can be regular or irregular and can include support members (e.g., flutes, bosses, posts, and the like) to maintain separation and a useable space between the shells. The space 52 can be configured as an annular space in accordance with an embodiment of the disclosure. In accordance with an embodiment of the disclosure, the space 52 can comprise a vacuum region or evacuated region. The vacuum space or evacuated region serves as an insulator, thereby reducing convection heat transfer phenomena.

In accordance with an embodiment of the disclosure, the ablation electrode assembly 10 further includes an irrigant distribution element 54. Irrigant distribution element 54 can be configured as a generally annular ring in accordance with an embodiment of the disclosure. The irrigation distribution element 54 has a proximal end 56 and a distal end 58. At least a portion of the proximal end 56 of the irrigant distribution element 54 can engage a catheter shaft in which the inner core member 14 can be located. At least a portion of the distal end 58 of the irrigant distribution element 54 can surround and/or encircle the inner core member 14 and, further, can define a circumferential irrigation port 60 between the irrigant distribution element 54 and the inner core member 14 in accordance with an embodiment of the disclosure. Irrigant distribution element 54 is configured to guide irrigation fluid toward outer shell 16 about and along outer surface 46 of the outer shell 16, and in particular, direct the fluid (e.g., irrigant) flow in a direction substantially parallel with the outer surface 46 of the outer shell 16. Irrigant distribution element 54 can include a fluid shaping member 61 that helps ensure that the fluid flow tends toward the surface 46 of the outer shell 16 of the ablation electrode assembly 10. For example and without limitation, the fluid shaping member 61 of the irrigant distribution element 54 can include a channel, rifling, boss, hump, chamfer, and/or combination thereof on a surface defining the circumferential irrigation port 60. The fluid shaping member 61 is configured to disturb fluid flow (e.g., cause fluid flowing closer to the outer surface of the inner core member 14 to slow down relative to fluid flowing farther from the outer surface of the inner core member 14), thereby helping to ensure that the fluid flow tends toward the surface 46 of the outer shell 16.

Figure 5:
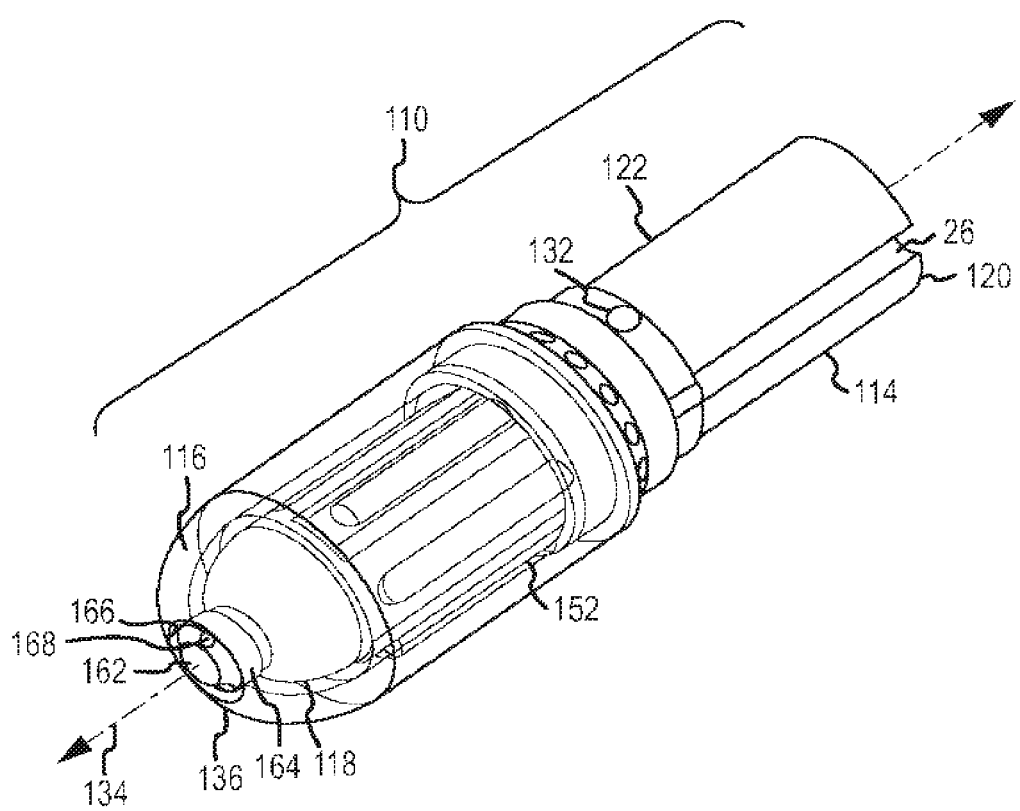
FIG. 5 is an isometric partially transparent view of an ablation electrode assembly in accordance with a second embodiment of the disclosure.
Figure 6:
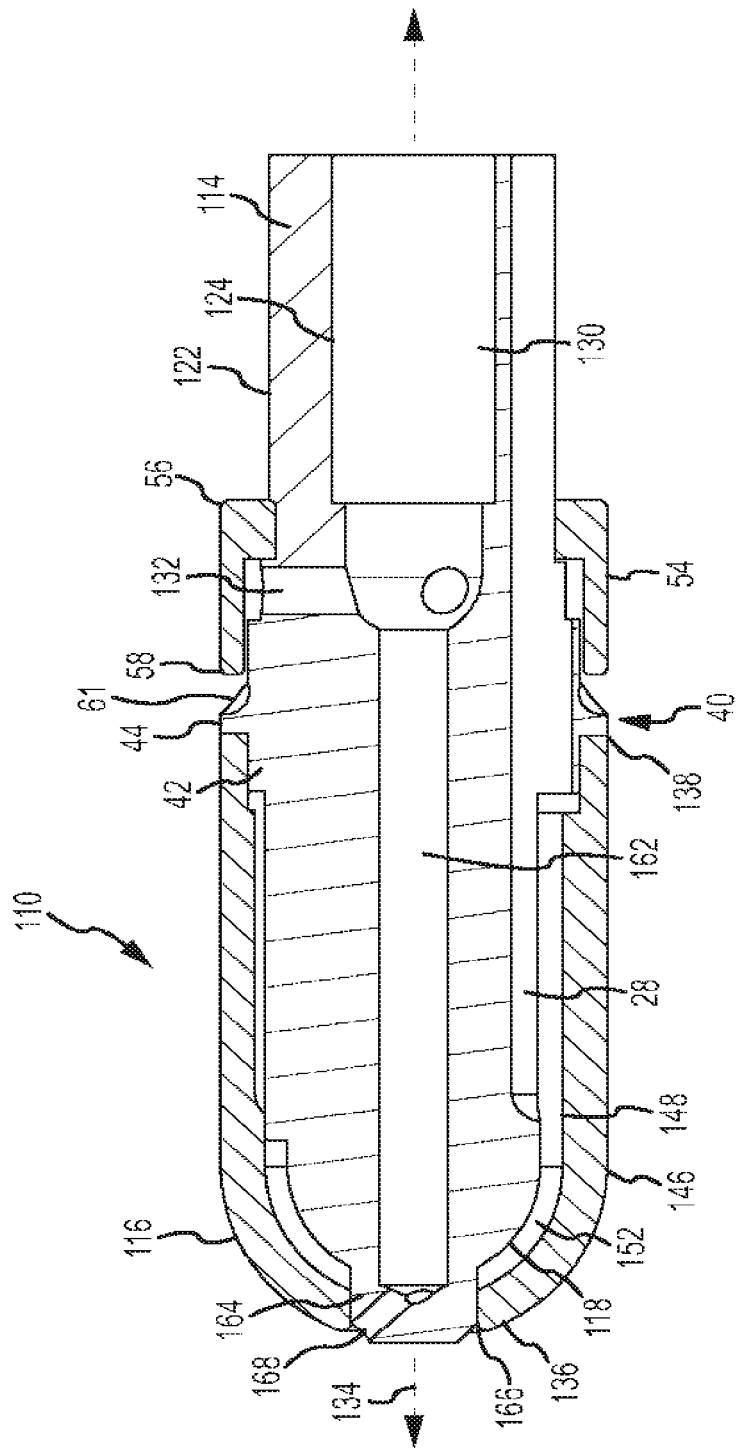
FIG. 6 is a cross-sectional view of the ablation electrode assembly of FIG. 4.

Referring now to FIGS. 5 and 6, the ablation electrode assembly 110 can include an inner core member 114 and an outer shell 116 in accordance with a second embodiment of the disclosure. The inner core member 114 and outer shell 116 of the ablation electrode assembly 110 in accordance with a second embodiment of the disclosure can be substantially identical to the inner core member 14 and outer shell 16 of the ablation electrode assembly 10 as described herein, except that the inner core member 114 and outer shell 116 can be modified to provide both proximal and distal delivery of irrigation fluid. The ablation electrode assembly 110 is configured to provide both proximal and distal delivery of irrigation fluid, can be especially beneficial to reduce thrombus formation and/or charring at the distal end (e.g., tip) of the ablation electrode assembly 110. By providing both proximal and distal delivery of irrigation fluid, it can further displace blood and prevent stasis in the areas adjacent the outer shell 116 of the ablation electrode assembly 110.

Ablation electrode assembly 110 is configured for distal delivery of irrigation fluid with an axially extending passageway 162 extending from the inner cavity 130 of the inner core member 114 to the distal end 118 of the inner core member 114. The inner core member 114 can further include a distal end portion 164 and the outer shell 116 can include an aperture 166 at distal end 136 of the outer shell 116. The distal end portion 164, coupled with aperture 166, can enable irrigation fluid flowing through the axially extending passageways 162 to flow to a distal end 136 (e.g., tip) of outer shell 116, therein substantially irrigating the distal end 136 (e.g., tip) of outer shell 116 of the ablation electrode assembly 110. Outer shell 16, 116 does not include any radially extending aperture in accordance with an embodiment of the disclosure. Distal end portion 164 can extend distally from the partially spherical and/or generally hemispherical distal end 118 of the inner core member 114 and can be generally cylindrical in shape. Distal end portion 164 can extend within the aperture 166 at distal end 136 of the outer shell 116. Distal end portion 164 can include one or more ports 168 extending from the axially extending passageway 162. For example and without limitation, distal end portion 164 can include three ports. Each of the ports 168 can be oriented at an acute angle (e.g., about 45 degrees) relative to the longitudinal axis 134 of the ablation electrode assembly 110. The orientation of the ports 168 varies depending on the design of the ablation electrode assembly 110. The ports 168 can be substantially equally spaced around the circumference of the distal end portion 164 in an embodiment. The axially extending passageway 162 extends through the distal end portion 164. Distal end portion 164 can comprise the same material as the inner core member 114. In other embodiments, the axially extending passageway 162 can extend directly through the distal end 36 of the outer shell 116.

In an embodiment of the disclosure, a coating (not shown) can be disposed on at least a portion of the inner core member 114 and/or outer core member 116 that defines the axially extending passageway 162. The coating can be comprised of an electrically non-conductive material. The coating can be comprised of diamond, diamond-like carbon (DLC) or polytetrafluoroethylene (PTFE), which is commonly sold by the E. I. du Pont de Nemours and Company under the trade name Teflon®. In an embodiment, the coating can be provided around the entire circumference and along the entire length of the axially extending passageway 162. However, the coating can be provided only around a portion of the circumference and/or only around a portion of the length of the axially extending passageway 162 in accordance with various embodiments of the disclosure. The amount of the coating provided around the circumference and/or length of the axially extending passageway 162 or portion thereof can vary depending on the relative requirements of ablation electrode assembly 110.

Figure 7:
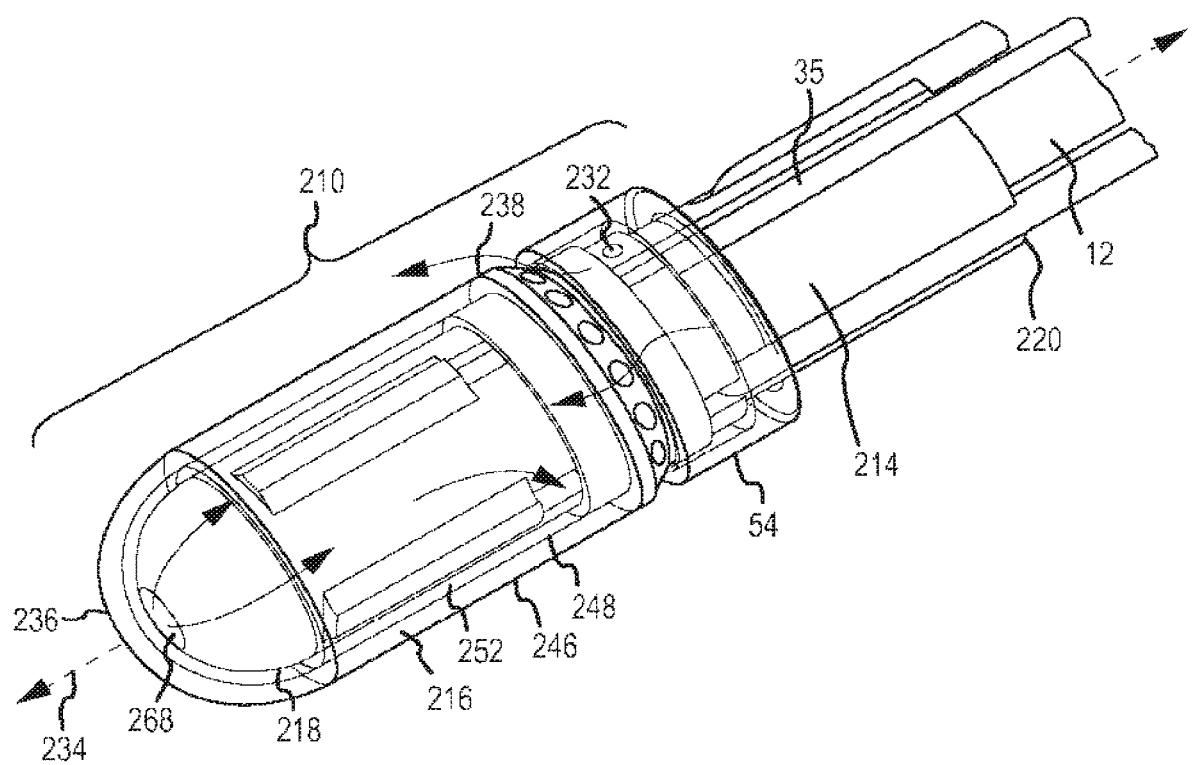
FIG. 7 is an isometric partially transparent view of an ablation electrode assembly in accordance with a third embodiment of the disclosure.
Figure 8:
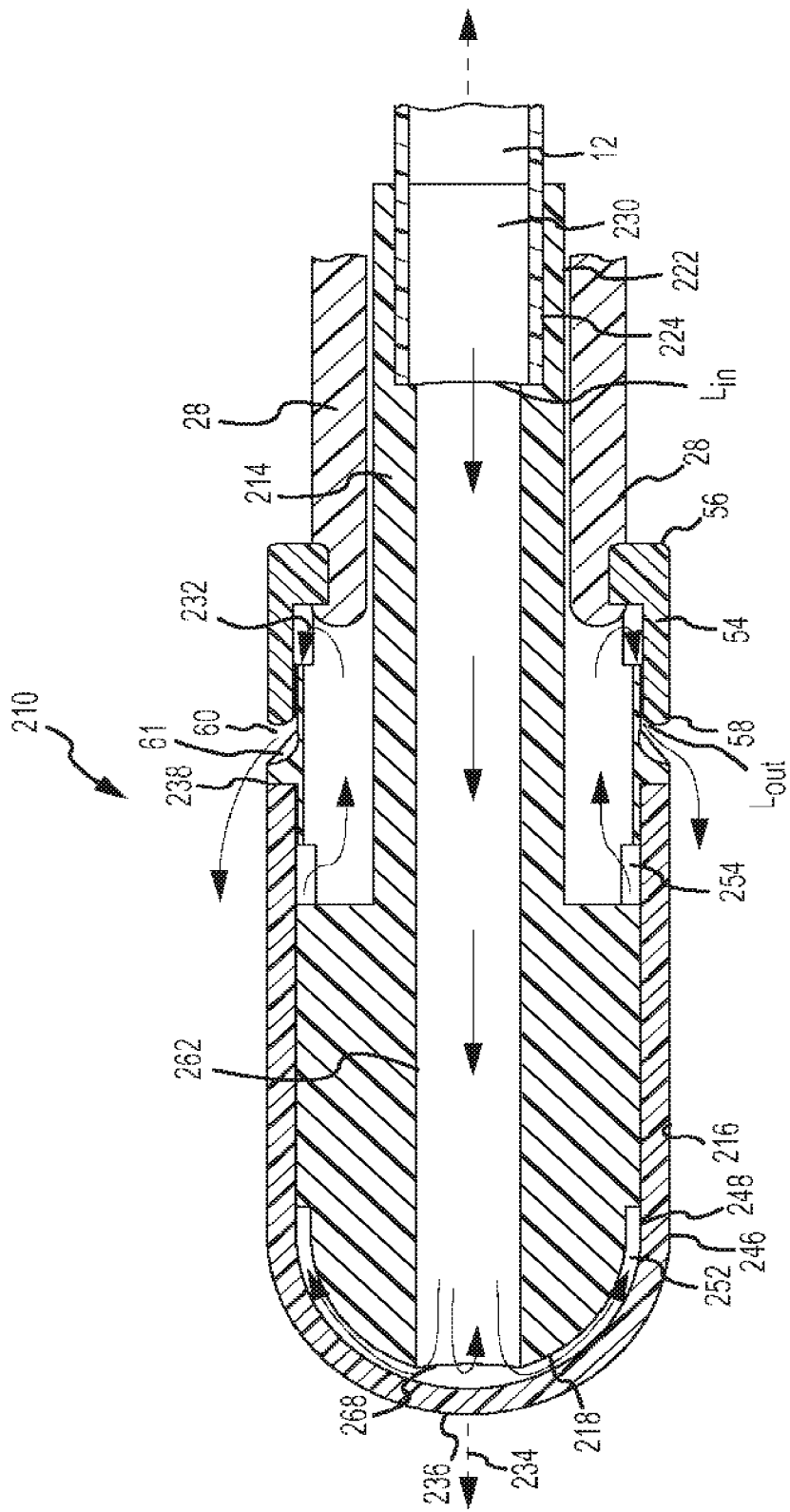
FIG. 8 is a cross-sectional view of the ablation electrode assembly of FIG. 6.

Referring now to FIGS. 7 and 8, the ablation electrode assembly 210 can include an inner core member 214 and an outer shell 216 in accordance with a third embodiment of the disclosure. The inner core member 214 and outer shell 216 of the ablation electrode assembly 210 in accordance with a third embodiment of the disclosure can be substantially identical to the inner core member 14 and outer shell 16 of the ablation electrode assembly 10 in accordance with a first embodiment of the disclosure as described herein, except that the inner core member 214 and outer shell 216 can be modified to allow for the flow of irrigation fluid in the annular space 252 between the inner core member 214 and outer shell 216.

Ablation electrode assembly 210 is configured for allowing the flow of irrigation fluid in the annular space 252 between the inner core member 214 and the outer shell 216 by including an aperture 268 located at the distal end 218 of the inner core member 214. The inner core member 214 also includes an axially extending passageway 262. The fluid delivery tube 12 can be in fluid communication with the axially extending passageway 262. The axially extending passageway 262 can terminate at aperture 268 located at the distal end 218 of the inner core member. Irrigation fluid from the axially extending passageway 262 can flow out of the aperture 268 in a first direction toward the distal end 236 of the outer shell 216. The irrigation fluid can then flow radially outwardly from the aperture 268 and can then eventually flow back in a second direction toward the proximal end 238 of the outer shell 216 in the annular space 252 between the outer shell 216 and the inner core member 214. The second direction can be opposite the first direction. Irrigation fluid flowing in the annular space 252 can absorb heat from both the circulating blood pool and the lesion being created in the targeted tissue during RF ablation. The irrigation fluid can then exit the annular space 252 between the outer shell 216 and the inner core member 214 and can flow through a collection channel 254 and then flow through a first radially extending passageway 232 of the inner core member 214. The first radially extending passageway 232 of the inner core member 214 can be similar to radially extending passageway 32 of inner core member 14, 114, except that the first radially extending passageway 232 cannot extend from the inner cavity 30 to the outer surface 22 of the inner core member 214. The first radially extending passageway 232 of the inner core member 214 instead extends from the collection channel 254 (and thus, the annular space 252), thereby allowing irrigation fluid that has flowed through the annular space 252 to exit the ablation electrode assembly 210. Delivery of irrigation fluid generally reduces char, thrombus formation, and coagulum formation, thereby enabling greater energy delivery during RF ablation. Delivery of irrigation fluid can also displace blood and prevent stasis in the areas adjacent the outer shell 216 of the ablation electrode assembly 210.

Accordingly, the annular space 252 is in fluid communication with both the inner cavity 230 of the inner core member 214 (e.g., through the axially extending passageway 262), as well as the first radially extending passageway 232. In an embodiment where the ablation electrode assembly 210 further includes irrigant distribution element 54, the distal end 58 of irrigant distribution element 54 can define a circumferential irrigation port 60 between the irrigant distribution element 54 and the inner core member 214. Irrigation fluid exiting the first radially extending passageway 232 can flow out the circumferential irrigation port 60 as best illustrated in FIG. 8.

Figure 9:
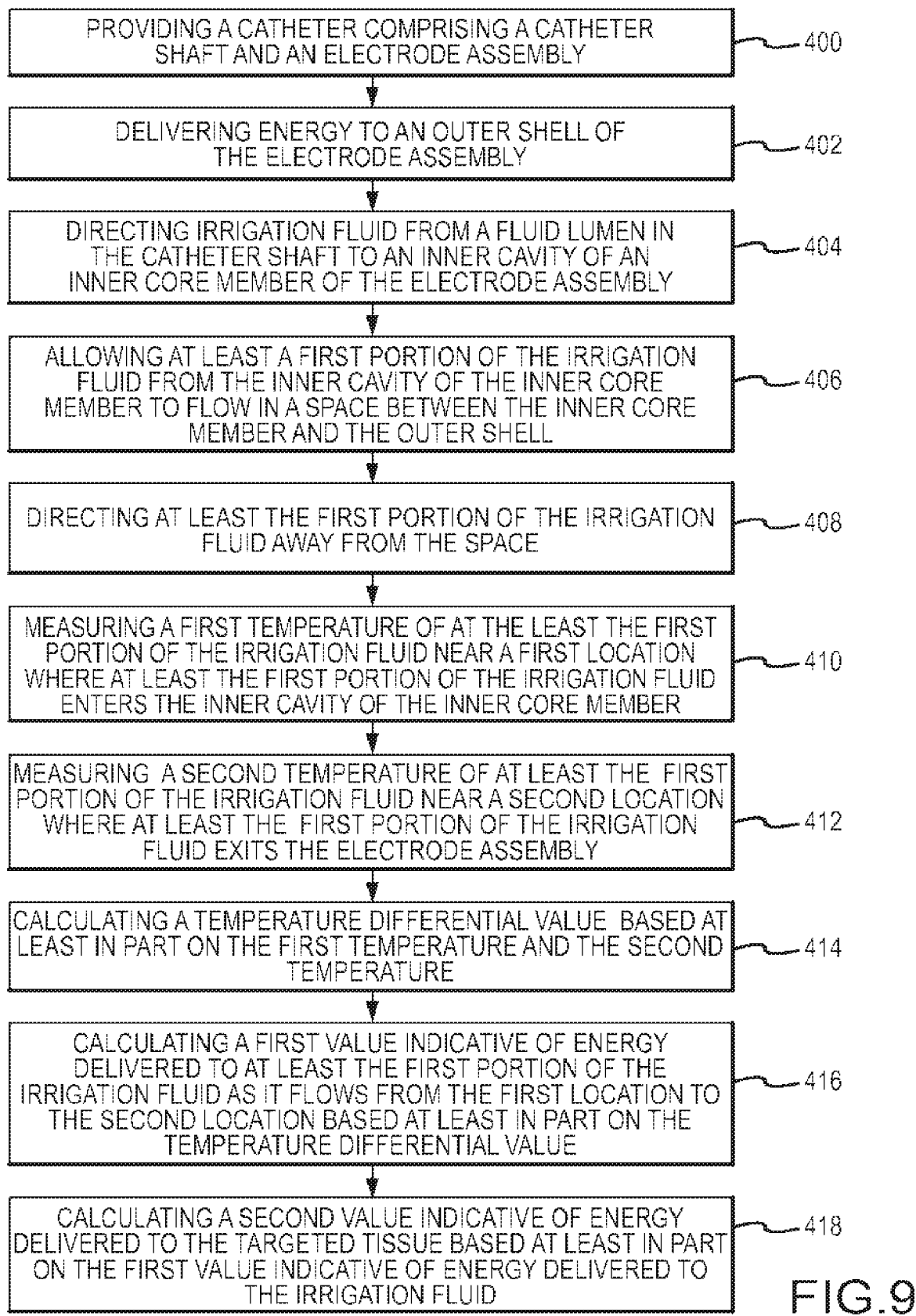
FIG. 9 is a flow diagram generally representing an exemplary method of using an ablation electrode assembly to control temperature during cardiac ablation of targeted tissue in accordance with a first embodiment of the disclosure.

FIG. 9 is a flow diagram generally representing an exemplary method of using an ablation electrode assembly 210 (or 310 as described hereinbelow) to provide irrigation fluid and/or control temperature during cardiac ablation of targeted tissue. In an embodiment of providing irrigation fluid during cardiac ablation of targeted tissue, a catheter is used in Step 400. The catheter can comprise a catheter shaft having a fluid lumen or fluid delivery tube 12 and an electrode assembly 210, 310 connected to the catheter shaft. The electrode assembly 210, 310 can include an inner core member 214, 314 having a distal end 218, 318 and a proximal end 220, 320. The inner core member 214, 314 can include an outer surface 222, 322 and an inner surface 224, 324. The inner surface can define an inner cavity 230, 330. The inner core member 214, 314 can further include a first radially extending passageway 232, 332 that extends through the outer surface 222 of the inner core member 214. The inner core member 214, 314 can further include an axially extending passageway 262, 362 extending from the inner cavity 230, 330 to the distal end 218, 318 of the inner core member 214, 314. The electrode assembly 210, 310 can further include an outer shell 216, 316 surrounding the inner core member 214, 314. The outer shell 216, 316 can have a distal end 236, 336 and a proximal end 238, 338. The ablation electrode assembly 210, 310 can further include plurality of thermal sensors 28. In an embodiment, the outer shell 216 can be scored with a plurality of axially extending grooves or slots 50 to separate the outer shell 216, 316 into a plurality of circumferentially-extending segments. In this embodiment, there can be a thermal sensor 28 for each of the plurality of segments of the outer shell 216, 316. Accordingly, each of the plurality of segments of the outer shell 216, 316 can have at least one corresponding thermal sensor 28 out of the plurality of thermal sensors 28. The inner core member 214, 314 and the outer shell 216, 316 can define an annular space 252, 352. Energy is delivered to the outer shell 216, 316 of the electrode assembly 210, 310 in Step 402. In particular, the outer shell 216, 316 of the electrode assembly 210, 310 is electrically connected to an ablation system 37 including an ablation generator 39 for generating and delivering energy to the catheter. The energy generated and delivered to the catheter 15 from the ablation generator 39 can be based at least in part on the highest temperature measurement from the plurality of thermal sensors 28 utilized in connection with the ablation electrode assembly 210, 310, both in embodiments where the outer shell 216, 316 is not separated into a plurality of segments and in embodiments where the outer shell 216, 316 is separated into a plurality of segments.

Irrigation fluid is directed from the fluid lumen or fluid delivery tube 12 to the inner cavity 30 of the inner core member 214, 314 in Step 404. At least a first portion of the irrigation fluid is allowed to flow from the inner cavity 30 of the inner core member 214, through the axially extending passageway 262 in the inner core member 214, and into the annular space 252 between the inner core member 214 and the outer shell 216 in Step 406. In accordance with one embodiment of the disclosure as generally illustrated in FIGS. 7 and 8, all of the irrigation fluid from the inner cavity 230 of the inner core member 214 (and thus all of the irrigation fluid delivered by the fluid delivery tube 12) can be directed from the inner cavity 230, through the axially extending passageway 262, and into the annular space 252. In accordance with other embodiments of the disclosure as generally illustrated in FIGS. 10 and 11, only a first portion of the irrigation fluid from the inner cavity 30 of the inner core member 314 (and thus only a portion of the irrigation fluid delivered by the fluid delivery tube 12) can be directed from the inner cavity 330, through the axially extending passageway 362, and into the annular space 352.

At least the first portion of the irrigation fluid from the inner cavity 230, 330 of the inner core member 214, 314 is directed away from the annular space 252, 352 between the inner core member 214, 314 and the outer shell 216, 316 in Step 408. As described above, in some embodiments all of the irrigation fluid from the inner cavity 230, 330 of the inner core member 214 can be directed into the annular space 252, 352, and so all of the irrigation fluid from the inner cavity 230, 330 of the inner core member 214, 314 can be directed from the annular space 252 in Step 408. In other embodiments, only first portion of the irrigation fluid from the inner cavity 230, 330 of the inner core member 214, 314 (and thus only a portion of the irrigation fluid delivered by the fluid delivery tube 12) can be directed away from the annular space 252, 352. In some embodiments, the first portion of the irrigation fluid is directed away from the annular space 252, 352 to the first radially extending passageway 232, 332. In other embodiments, the first portion of the irrigation fluid is directed away from the annular space 252, 352 toward a proximal end of the catheter for elimination from the catheter at a location that is remote from a patient.

Figure 10:
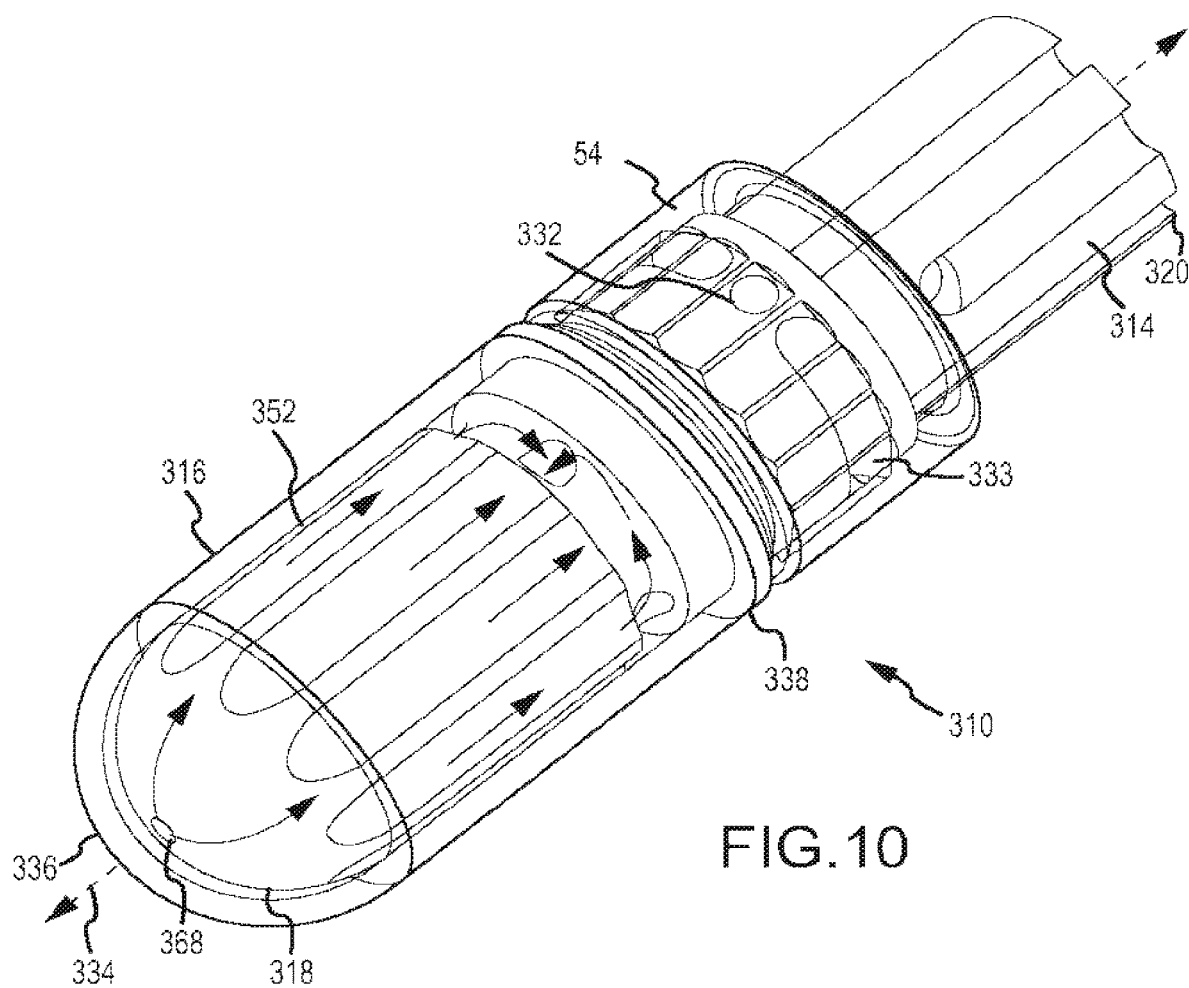
FIG. 10 is an isometric partially transparent view of an ablation electrode assembly in accordance with a fourth embodiment of the disclosure.
Figure 11:
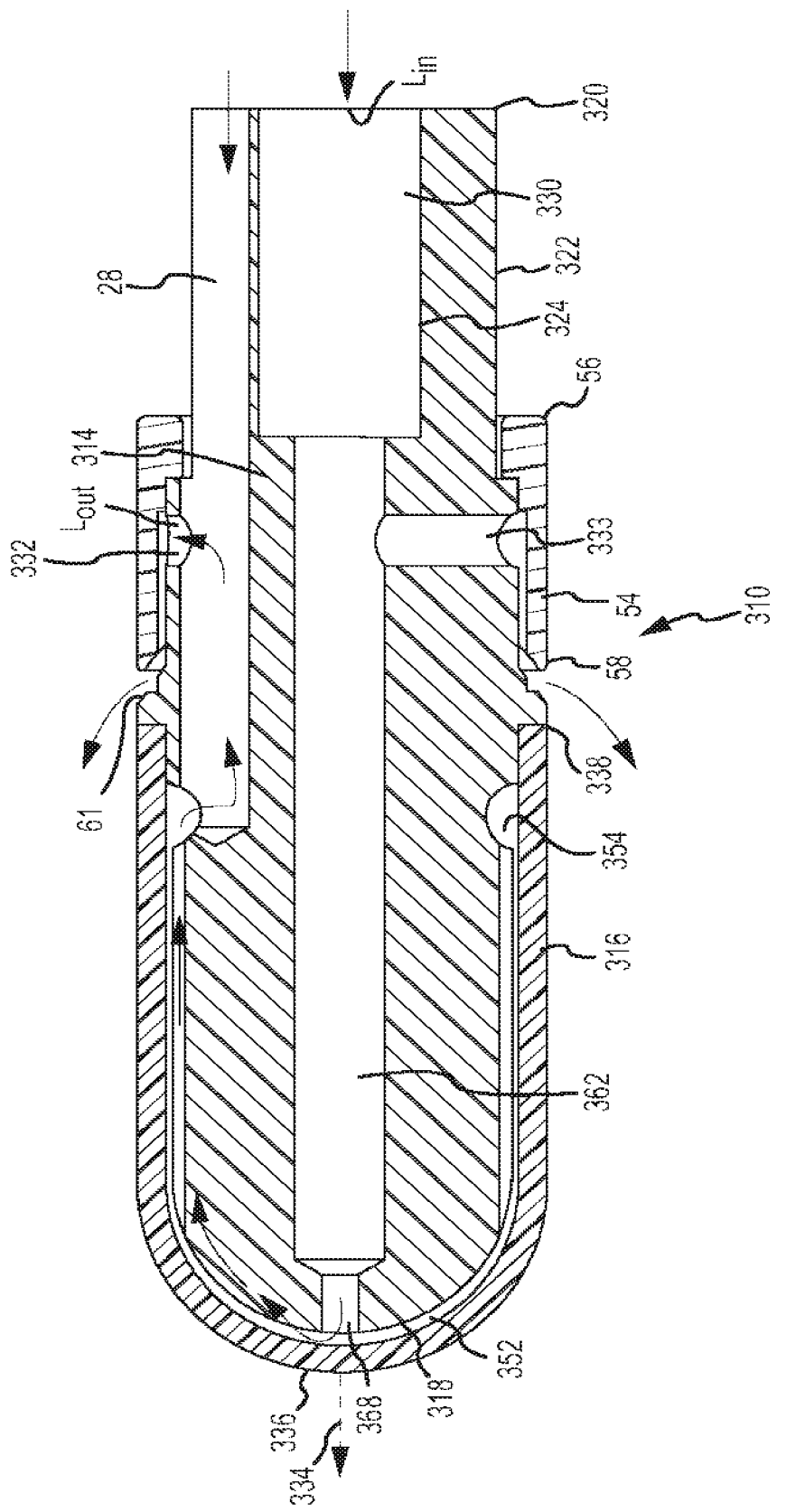
FIG. 11 is a cross-sectional view of the ablation electrode assembly of FIG. 7.

In the embodiments where only a first portion of the irrigation fluid from the inner cavity 230, 330 of the inner core member 214, 314 is directed to the annular space 252, 352 and to the first radially extending passageway 232, 332 or toward the proximal end of the catheter for elimination from the catheter at a location that is remote from a patient, the inner core member 214, 314 includes a second radially extending passageway 333 as illustrated in FIGS. 10 and 11. The second radially extending passageway 333 extends from and is in direct fluid communication with the inner cavity 330 to the outer surface 322 of the inner core member 314. The second radially extending passageway 333 of the inner core member 314 can be similar to radially extending passageway 32, 132 of inner core member 14, 114. In accordance with this embodiment of the disclosure as generally illustrated in FIGS. 10 and 11, fluid that has flowed through the axially extending passageway 362 and/or the annular space 352 does not flow through the second radially extending passageway 333 and instead flows through the first radially extending passageway 332 as described hereinabove. At least a second portion of the irrigation fluid from the inner cavity 330 of the inner core member 314 can be directed directly to the second radially extending passageway 333, thereby allowing for proximal delivery of irrigation fluid. Delivery of irrigation fluid generally reduces char, thrombus formation, and coagulum formation, thereby enabling greater energy delivery during RF ablation. Delivery of irrigation fluid can also displace blood and prevent stasis in the areas adjacent the outer shell 316 of the ablation electrode assembly 310. In accordance with an embodiment of the disclosure, the irrigation fluid can comprise ultra-cold saline. The use of ultra-cold saline can be advantageous in providing increased cooling of tissue to reduce char, thrombus formation, and coagulum formation. The first portion of the irrigation fluid (that is directed to the annular space 352 and to the collection channel 354 and to the first radially extending passageway 332) can be separate from the second portion of the irrigation fluid (that is directed to the second radially extending passageway 333).

The irrigation fluid flowing in the annular space 252, 352 can absorb heat from the circulating blood pool and the lesion being developed at the targeted tissue during RF ablation in which energy is delivered to the outer shell 216, 316 of the electrode assembly 210, 310. By monitoring the change in temperature of the irrigation fluid as it flows through the annular space 252, 352, it can be possible to estimate the energy removed from the ablation electrode assembly 210, 310 during an ablation cycle, thereby making it possible to better estimate the energy actually delivered to the targeted tissue. Typically, irrigation fluid is at or about room temperature (e.g., about 23)° ° C. In accordance with an embodiment of the disclosure, the irrigation fluid for use with the electrode assembly 210, 310 can be preheated to biological temperature. Biological temperature generally means near or above normal body temperature (e.g., about 37° C. or above). While preheated irrigation fluid at temperatures above about 37° C. are mentioned herein, the preheated irrigation fluid will not exceed a predetermined threshold in accordance with an embodiment of the disclosure. The predetermined threshold can vary in accordance with embodiments of the invention. In general, the temperature of the irrigation fluid will not exceed the temperature of the targeted tissue 13. Preheating of the irrigation fluid to biological temperature can be advantageous in connection with monitoring the change in temperature of the irrigation fluid as it flows through the annular space 252, 352. In particular, preheating of the irrigation fluid may help ensure that any increase in temperature of the irrigation fluid as it flows through the ablation electrode assembly 210, 310 is due to the application of energy from the ablation electrode assembly 210, 310, and not simply due to warming of the irrigation fluid by blood and/or tissue. Preheating of the irrigation fluid can thus result in an improved estimate of the energy removed from the ablation electrode assembly 210, 310 during an ablation cycle, which in turn can result in an improved estimate of the remaining energy being delivered to the targeted tissue.

In accordance with the embodiment of the ablation electrode assembly 310 generally illustrated in FIGS. 10 and 11, the flow rate of the second portion of the irrigation fluid (that is directed to the second radially extending passageway 333) can be greater than the flow rate of the first portion of the irrigation fluid (that is directed to the annular space 352 and to the collection channel 354 and to the first radially extending passageway 332). For example and without limitation, the flow rate of irrigation fluid from the fluid delivery tube 12 can be approximately 6-10 ml/minute, and the flow rate of the first portion of the irrigation fluid can be only approximately 1-3 ml/minute. In particular, aperture 368 can be configured to allow a flow rate for irrigation fluid of approximately 1-3 ml/minute. Accordingly, the majority of the irrigation fluid delivered by the fluid delivery tube 12 can be directed out of the second radially extending passageway 333. The flow rate of the second portion of the irrigation fluid can be approximately 3-9 ml/minute. Although these flow rates are mentioned herein, the various flow rates can be greater or smaller in accordance with other embodiments of the disclosure. In this way, only a relatively small amount of irrigation fluid from the fluid delivery tube 12 is directed through the outer shell 316 of the ablation electrode assembly 310, while the majority of the irrigation fluid from the fluid delivery tube 12 is ejected out of the irrigant distribution element 54. Accordingly, ablation electrode assembly 310 allows for the additional steps of measuring temperatures of at least a first portion of the irrigation fluid as described in more detail below, while providing a higher secondary flow rate of irrigation fluid that is sufficient to flush the surface of the ablation electrode assembly 310 and displace blood at the lesion site in the targeted tissue. Irrigation fluid directed to the second radially extending passageway 333 with the irrigant distribution element 54 can help reduce charring and inhibit the formation of coagulum and/or soft thrombus by mixing, displacing and/or diluting blood that can be in contact with ablation electrode assembly 310.

In some embodiments, the overall total fluid volumes associated with the flow rate of the first portion of the irrigation fluid combined with the flow rate of the second portion of the irrigation fluid can be much lower than prior art or typically utilized in clinical practice. That is, overall total fluid volume can range from low single digits to less than about two or so milliliters per minute (ml/min) while effectively reducing or eliminating char and coagulum and improving temperature correlation for more precise control of temperature during ablation procedures. In an embodiment, overall total fluid volume delivered to a patient can be well below about seven or so ml/min or less. Such low overall total fluid volumes can be especially valuable for patients already suffering from fluid overload (e.g., patient having heart failure and the like). Of course, for patients that can tolerate fluid intake or for procedures seeming to require higher fluid delivery rates or volumes, the embodiments herein can accommodate same.

A first temperature $T_{in}$ of at least the first portion of the irrigation fluid is measured at a first location $L_{in}$ near where at least the first portion of the irrigation fluid enters the inner cavity 230, 330 of the inner core member 214, 314 and/or where at least the first portion of the irrigation fluid enters the axially extending passageway 262, 362 from the inner cavity 230, 330 in Step 410. A first thermal sensor 28 is used to measure the first temperature $T_{in}$. A second temperature $T_{out}$ of at least the first portion of the irrigation fluid is measured at a second location Lout near where at least the first portion of the irrigation fluid exits the electrode assembly 210, 310 in Step 412. In one embodiment, the second location can be near where at least the first portion of the irrigation fluid exits the radially extending passageway 232, 332. In other embodiments, the second location can be near where at least the first portion of the irrigation fluid exits the electrode assembly 210, 310 for eventual elimination from the catheter at a location remote from a patient. A second thermal sensor 28 is used to measure the second temperature $T_{out}$.

A temperature differential value $\Delta T$ is calculated based at least in part on the first temperature $T_{in}$ and the second temperature $T_{out}$ in Step 414. An electronic control unit (ECU) 45 can be in connection with the thermal sensors 28 and can be used to calculate the temperature differential value. A display device 47 can also be used in connection with the ablation electrode assembly 210, 310 and ECU 45. The ECU 45 preferably comprises a programmable microprocessor or microcontroller, but can alternatively comprise an application specific integrated circuit (ASIC). The ECU 45 can include a central processing unit (CPU) and an input/output (I/O) interface through which the ECU 45 can receive input data (e.g., temperature measurements from thermal sensors 28) and can generate output data (e.g., temperature differential value $\Delta T$). The temperature differential value $\Delta T$ is calculated in accordance with the following equation:

$$\Delta T = (T_{out} - T_{in}) \quad \text{(Equation 1)}$$

A first value $Q_1$ indicative of energy delivered to at least the first portion of the irrigation fluid as it flows from the first location (where the irrigation fluid enters the inner cavity 230, 330 of the inner core member 214, 314 and/or where the irrigation fluid enters the axially extending passageway 262, 326 from the inner cavity 230, 330) to the second location (where the irrigation fluid exits the radially extending passageway 232, 332) is calculated based at least in part on the temperature differential value $\Delta T$ in Step 416. The ECU 45 can be used to calculate the first value $Q_1$. The first value $Q_1$ is calculated in accordance with the following equation, where m=mass of the irrigation fluid and Cp=specific heat of the irrigation fluid.

$$Q_1 = m \; Cp(T_{out} - T_{in}) \quad \text{(Equation 2)}$$

The catheter 15 to which the ablation electrode assembly 210, 310 can be connected can include a memory such as an EEPROM that stores numerical values for the coefficient (e.g., specific heat of the irrigation fluid referred to as Cp in Equation 2) or stores a memory address for accessing the numerical values in another memory location (either in the catheter EEPROM or in another memory). The ECU 45 can also have a memory. The ECU 45 can retrieve these values or addresses directly or indirectly from the memory of the catheter 15 or the ECU 45. The input data and output data acquired and generated by the ECU 45 can also be stored in the memory of the catheter 15 or the ECU 45. As described above, the input data can include the first and second temperatures $T_{in}$ and $T_{out}$ obtained by the thermal sensors 28. The input data can further include information regarding the flow rate of irrigation fluid obtained from a control system 49 and described in more detail below. The flow rate can be used to obtain information regarding the mass of the irrigation fluid referred to as m in Equation 2. As described above, the output data can include the temperature differential value $\Delta T$ and/or the first value $Q_1$.

A second value $Q_2$ indicative of energy delivered to the targeted tissue is calculated based at least in part on the first value $Q_1$ in Step 418. The ECU 45 can be used to calculate the second value $Q_2$. The second value $Q_2$ is calculated in accordance with the following equation, where E=electrical energy provided to the ablation electrode assembly 210, 310 (E=P×t, where P=power and t=time):

$$Q_2 = E - Q_1 \quad \text{(Equation 3)}$$

The output data can further include the second value $Q_2$. The delivery of energy to ablation electrode assembly 210, 310 is preferably controlled by the control system 49. The control system 49 is configured to determine the temperature of the tissue to be ablated and/or an appropriate ablation technique. The outer shell 216, 316 of the ablation electrode assembly 210, 310 is connected to the control system 49 with wires. The ablation generator 39 can form part of the control system 49 or can be separate from the control system 49 in other embodiments. Thermal sensors 28 are also connected to the control system. For example and without limitation, wires can extend through lumens in the catheter. Devices for determining pressure, temperature, and a flow parameter of a flowing fluid available from Radi Medical Systems AB, and as generally shown with reference to at least U.S. Pat. No. RE39,863 entitled "Combined flow, pressure and temperature sensor," the entire disclosure of which is incorporated herein by reference can be used to monitor and/or control the quantity of flow of irrigation fluid within or from the catheter at one or more locations using a flow-from pressure algorithm. These devices for determining pressure, temperature, and a flow parameter of a flowing fluid are also connected to the control system. The ECU 45 and display device 47 can also be connected to the control system 49.

The control system 49 can be configured to adjust the amount of energy E generated and delivered to the catheter 15 from the ablation generator 39 based at least in part on the temperature differential value $\Delta T$ in accordance with an embodiment of the disclosure. For example, a greater temperature differential value ΔT suggests that more energy is being removed from the ablation electrode assembly 210, 310, such that the ablation generator 39 can be configured to provide more energy to the ablation electrode assembly 210, 310. The energy provided to the ablation electrode assembly 210, 310 can be increased by increasing the power and/or the length of time of energy delivery (e.g., frequency and/or operating time) during the ablation cycle. For example, a lower temperature differential value ΔT suggests that less energy is being removed from the ablation electrode assembly 210, 310, such that the ablation generator 39 can be configured to provide less energy to the ablation electrode assembly 210, 310. The energy provided to the ablation electrode assembly 210, 310 can be decreased by decreasing the power and/or length of time of energy delivery (e.g., frequency and/or operating time) during the ablation cycle.

The temperature differential value ΔT for the irrigation fluid can be correlated to the actual temperature of the targeted tissue during RF ablation, and data regarding the correlation between the temperature differential value ΔT and the actual temperature of the targeted tissue can be stored by the ECU 45 or memory of catheter 15. The correlation between the temperature differential value ΔT and the actual temperature of the targeted tissue 13 can be determined by utilization of the thermal properties and flow rates of the irrigation fluid to obtain information regarding the energy state of the targeted tissue 13 that is part of the external environment. In this way, the control system 49 can be configured to use the temperature differential value ΔT for the irrigation fluid in order to estimate the temperature of the targeted tissue 13 (or the interface between the ablation electrode assembly 210, 310 and the targeted tissue 13) and ultimately select an appropriate ablation technique. The ablation technique that is selected can be selected to produce a certain, predetermined temperature in the targeted tissue 13 that will form a desired lesion in the targeted tissue. While the desired lesion can be transmural in some embodiments, the characteristics of the desired lesion can vary significantly. The certain, predetermined temperature in the targeted tissue 13 that will form a desired lesion in the targeted tissue 13 can be affected by the thermal response of the targeted tissue. The thermal response of the targeted tissue 13 can be affected by a number of variables including tissue thickness, amount of fat and muscle, blood flow through the region, and blood flow at the interface of the ablation electrode assembly 210, 310 and the targeted tissue 13.

Figure 12:
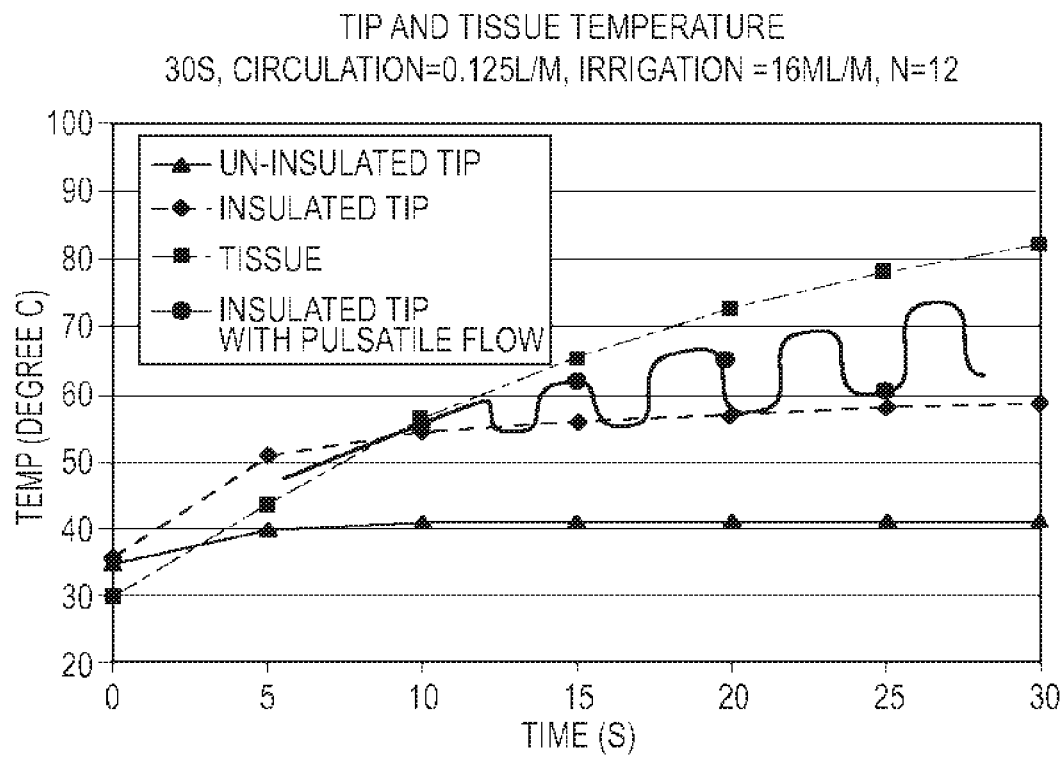
FIG. 12 is a chart comparing the temperature of the distal end portion of ablation electrode assemblies and the temperature of the targeted tissue over time.

FIG. 12 is an exemplary chart comparing the temperature of the distal end portion of ablation electrode assemblies with the temperature of the targeted tissue over time. As generally illustrated in FIG. 12, the temperature recorded at the distal end portion of ablation electrode assemblies typically lags that of the targeted tissue. Moreover, the temperature recorded at the distal end portion of ablation electrode assemblies plateaus, resulting in an even more significant difference from the temperature of the targeted tissue. Difference between the temperature recorded at the distal end portion of ablation electrode assemblies and targeted tissue is most acute in connection with ablation electrode assemblies that are un-insulated. Although ablation electrode assemblies having an insulated tip (including ablation electrode assemblies 10, 110, 210, 310) have an improved correlation between the temperatures of the distal end portion of the ablation electrode assemblies 10, 110, 210, 310 with the temperatures of the targeted tissues as generally illustrated in FIG. 12, RF ablation would benefit from an even more improved correlation between the temperatures of ablation electrode assemblies and targeted tissues.

Figure 13:
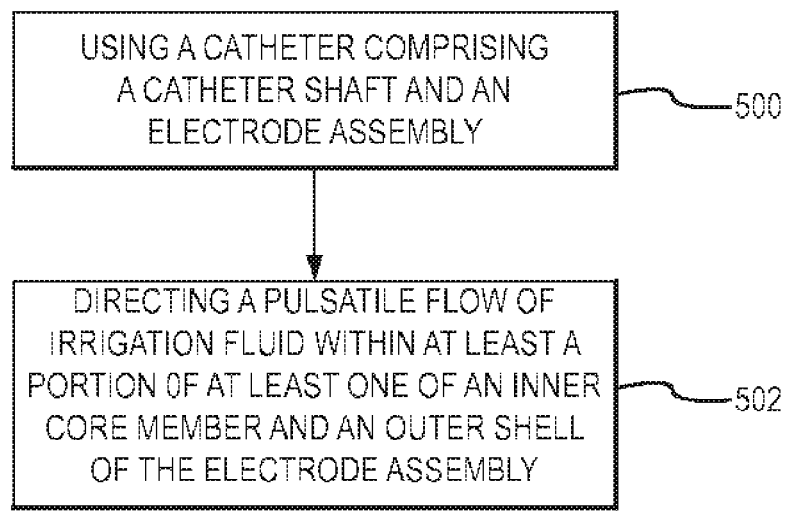
FIG. 13 is a flow diagram generally representing an exemplary method of using an ablation electrode assembly to control temperature during cardiac ablation of targeted tissue in accordance with a second embodiment of the disclosure.

FIG. 13 is a flow diagram generally representing an exemplary method of using an ablation electrode assembly 10, 110, 210, 310 to provide irrigation fluid during cardiac ablation of targeted tissue in an effort to further improve the correlation between the temperatures of the distal end portions of ablation electrode assemblies 10, 110, 210, 310 and the targeted tissues. In particular, a pulsatile flow of irrigation fluid can be utilized to increase flow turbulence and help prevent stagnation areas. Although pulsatile flow is mentioned herein in accordance with some embodiments of the invention, ablation electrode assemblies 10, 110, 210, 310 can be used in connection with any type of flow of irrigation fluid. For example and without limitation, pulsatile flow, intermittent flow, constant flow, and/or variable flow of irrigation fluid can be used in connection with ablation electrode assemblies 10, 110, 210, 310.

In an embodiment of providing irrigation fluid during cardiac ablation of targeted tissue, a catheter is used in Step 500. The catheter 15 can comprise a catheter shaft 17 having a fluid lumen or fluid delivery tube 12 and an electrode assembly 10, 110, 210, 310 connected to the catheter shaft. The electrode assembly 10, 110, 210, 310 can include an inner core member 14, 114, 214, 314 and an outer shell 16, 116, 216, 316. The inner core member 14, 114, 214, 314 and the outer shell 16, 116, 216, 316 can define an annular space 52, 152, 252, 352 therebetween. In accordance with an embodiment of the disclosure, a pulsatile flow of irrigation fluid can be directed within at least a portion of at least one of the inner core member 14, 114, 214, 314 and outer shell 16, 116, 216, 316 in Step 502. The irrigation fluid has a first flow rate in a first time period and has a second flow rate in a second time period. The first flow rate and the second flow rate can alternate and recur at intervals over time. The first flow rate and the second flow rate can alternate and recur at regular intervals in accordance with some embodiments of the disclosure and/or can alternate and recur at irregular intervals in accordance with other embodiments of the disclosure. The first flow rate and the second flow rate can be intermittent in an embodiment of the disclosure. In accordance with an embodiment of the disclosure, the second flow rate is greater than the first flow rate. For example and without limitation, the first flow rate can be approximately 2 ml/min, and the second flow rate can be approximately 13 ml/min. In accordance with other embodiments of the disclosure, the first flow rate can be greater than the second flow rate. Accordingly, the irrigation fluid is a pulsatile flow in alternating waves of low flow rates and high flow rates, where either a low flow rate occurs first or a high flow rate occurs first. Utilization of a first flow rate of irrigation fluid that is higher and a second flow rate of irrigation fluid that is lower can be preferred in some stepped irrigation sequences. Although these particular flow rates are mentioned herein, the first and second flow rates can be smaller or greater in other embodiments of the disclosure.

The use of a pulsatile flow rate allows the temperature measurement from the thermal sensors 28 at the outer shell 16, 116, 216, 316 of the ablation electrode assembly 10, 110, 210, 310 as described herein to increase temporarily during a first time period with a lower first flow rate, thereby bringing the temperature measurement from the thermal sensors 28 closer to the actual temperature of the interface between the ablation electrode assembly 10, 110, 210, 310 and the targeted tissue 13 so that the thermal sensors 28 more closely reflect the actual temperature. In particular, the method of using an ablation electrode assembly 10, 110, 210, 310 to control temperature during cardiac ablation of targeted tissue 13 can utilize an extended period of low flow early in the power delivery ablation cycle in order to provide a so-called "warm-up" sequence. The use of a pulsatile flow with an ablation electrode assembly 10, 110, 210, 310 having an inner core member 14, 114, 214, 314 and an outer shell 16, 116, 216, 316 can benefit most from the wave(s) of lower flow rates because the ablation electrode assembly 10, 110, 210, 310 already has an improved correlation between the temperatures of the ablation electrode assemblies 10, 110, 210, 310 and the targeted tissue. During a second time period with a higher second flow rate, the ablation electrode assembly 10, 110, 210, 310 best receives the benefits of tissue cooling and coagulum reduction. Accordingly, the method of using an ablation electrode assembly 10, 110, 210, 310 to control temperature during cardiac ablation of targeted tissue can utilize higher flow rates to reduce the temperature of the interface between the electrode ablation assembly 10, 110, 210, 310 and the targeted tissue. In an exemplary embodiment of the disclosure, the method of using an ablation electrode assembly 10, 110, 210, 310 to control temperature during cardiac ablation of targeted tissue can employ the following pattern of flow rates: (1) an initial warm-up period; (2) a first flow rate (e.g., 2 ml/min) for a first time period (e.g., 6 seconds); (3) a first cool-down period; (4) a second flow rate (e.g., 13 ml/min) for a second time period (e.g., 4 seconds); (5) a recovery period; (6) a first flow rate (e.g., 2 ml/min) for a first time period (e.g., 6 seconds); (6) a second cool-down period; and (7) a second flow rate (e.g., 13 ml/min) for a second time period (e.g., 4 seconds). Pulsatile flow of irrigation fluid can also help prevent stagnation areas and increase flow turbulence, which can help prevent stasis and the formation of coagulum.

Valve members, for example and without limitation, such as those shown and described in co-owned U.S. Patent Application Publication No. 2008/0161795, or other similar flow control features can be used in connection with catheters incorporating ablation electrode assemblies 10, 110, 210, 310 in order to alternate between first and second flow rates. In other embodiments, the flow control features can be part of an ancillary control system separate from and to be used in conjunction with catheters. The valves can operate automatically without user input and/or can operate based on feedback recorded during RF ablation by the ECU 45. The feedback can relate to time, temperature, and/or impedance, for example and without limitation. For example, the first and second flow rates can be based at least in part on temperature measurements taken by the thermal sensors 28. For example, as temperature measurements from thermal sensors 28 increase, a higher flow rate can be desirable. For another example, as temperature measurements from thermal sensors 28 decrease, a lower flow rate can be desirable. The thermal sensors 28 can thus provide feedback which can be implemented in a control algorithm executed by the ECU 45 and/or control system 49 to automatically control the flow rates of irrigation fluid within catheters incorporating ablation electrode assembly 10, 110, 210, 310. For example, the first and second flow rates can be based at least in part on an impedance measurement taken by a positioning electrode as described hereinabove. In particular, the positioning electrodes can be used to sense an impedance at a particular location and transmit a representative signal to the ECU 45 (or another external computer or processor). Circuitry for implementing the feedback automatically in a control algorithm can be readily provided by those having ordinary skill in the art after becoming familiar with the teachings herein. Although pulsatile flow of irrigation fluid is mentioned and described herein, other flow patterns for irrigation fluid (e.g., intermittent, constant, variable) can be used in connection with other embodiments of the invention.

Stepped irrigation sequences utilize varying flow rates of irrigation fluid, which can provide advantages as compared to an irrigation sequence utilizing a constant flow rate of irrigation fluid during an ablation cycle. As described hereinabove, utilization of a first flow rate of irrigation fluid that is higher and a second flow rate of irrigation fluid that is lower can be particularly advantageous. In accordance with an embodiment of the disclosure, a system 11 includes an irrigated catheter 15. A higher flow rate of irrigation fluid is delivered to the irrigated catheter 15 in a first period of time, and a lower flow rate of irrigation fluid is delivered to the irrigated catheter 15 in a second period of time. This particular sequence of irrigation fluid delivery can improve correlation between the measured temperature of the tip of the irrigated catheter 15 and the actual temperature of the targeted tissue 13. Although only a first flow rate in a first time period and a second flow rate in a second time period is described and illustrated, there can be more than two flow rates and more than two time periods in accordance with the invention. Utilization of more than two different flow rates and/or more than two time periods can provide clinical advantages in accordance with some embodiments of the invention. For example, intermittent cycling between higher and lower flow rates can result in corresponding intermittent cycling between higher and lower power levels as described in more detail below.

A higher power level during the first time period can help to increase lesion size and provide an overall increase in the total energy delivered during an ablation cycle. The lower power level during the second time period allows for continued energy delivery at a lower rate to essentially provide a "cool down" period. In addition, a higher power level during the first time period is believed to advantageously or beneficially change the electrical and/or thermal characteristics of the targeted tissue 13. In particular, it is believed that an initial higher power delivery "conditions" the targeted tissue 13, thereby inhibiting continuing increases in the temperature of the targeted tissue over the entire duration of an RF ablation cycle. Accordingly, the system 11 provides favorable conditions within the targeted tissue 13 for subsequent power delivery, thereby mitigating adverse affects of sustained power delivery such as overheating of the targeted tissue 13 and/or tissue or steam pop.

In accordance with this embodiment of the disclosure, the irrigated catheter 15 can comprise an irrigated catheter having a catheter shaft 17 having a fluid lumen or fluid delivery tube 12 in fluid communication with a source 21 of irrigation fluid; an electrode assembly 10, 110, 210, 310 connected to the catheter shaft 17; and at least one thermal sensor 28 disposed within the catheter 15 as described hereinabove. In other embodiments of the disclosure, other irrigated catheters and/or electrode assemblies can be used in connection with irrigation sequences having a first flow rate of irrigation fluid that is higher and a second flow rate of irrigation fluid that is lower. In accordance with an embodiment of the disclosure, the system 11 can further include an ablation generator 39, an ECU 45, and a control system 49.

The ablation generator 39 is configured to generate, deliver, and control ablation energy (e.g., RF) output by the ablation electrode assembly 10, 110, 210, 310 of the irrigated catheter 15. As described hereinabove, any number of various other catheters and/or ablation electrode assemblies can be utilized in connection with system 11 in accordance with other embodiments of the disclosure.

The ECU 45 can be operatively connected to the thermal sensor 28, the source 21 of irrigation fluid, and the ablation generator 39. The ECU 45 can be configured to receive as an input temperature measurement data from the thermal sensor 28. The ECU 45 can be further configured to determine a power delivery rate value for the ablation generator 39. The power delivery rate value for the ablation generator 39 can be responsive to the temperature measurement data. The ECU 45 can be further configured to provide an output signal corresponding to the power delivery rate value. In particular, the ECU 45 can provide the output signal to the control system 49.

Figure 14:
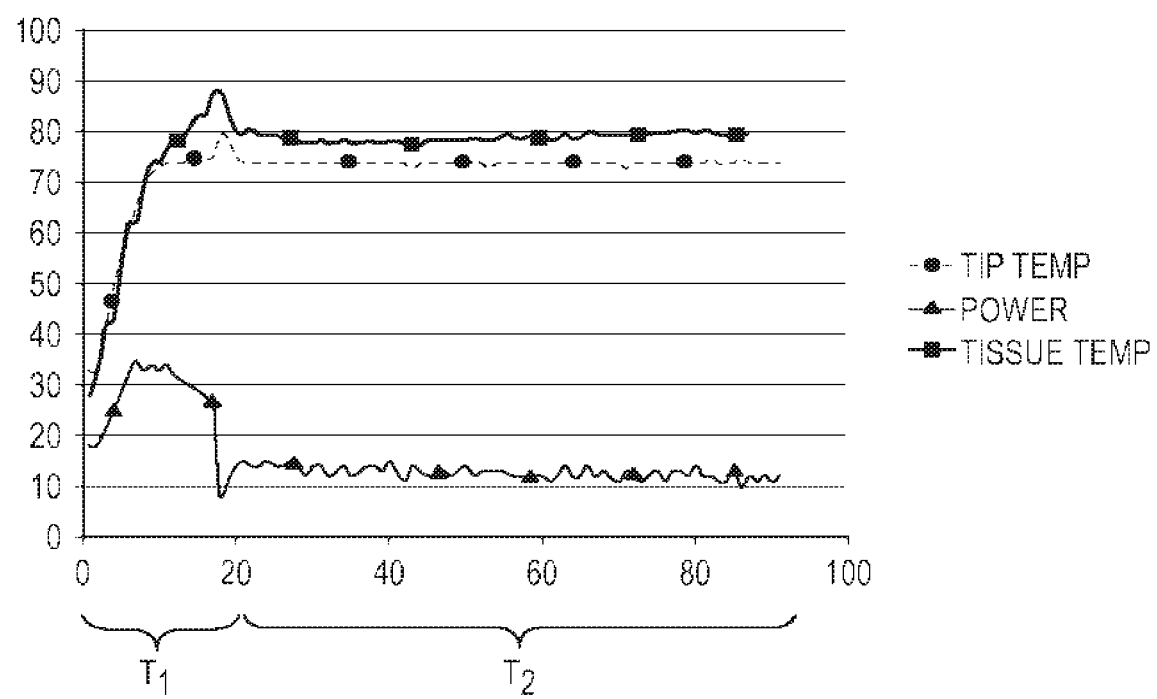
FIG. 14 is a chart comparing the temperature of the distal end portion of an ablation electrode assembly of an irrigated catheter, the temperature of targeted tissue, and power delivered by an ablation generator connected to the irrigated catheter over time in accordance with an embodiment of the disclosure.

In accordance with an embodiment of the disclosure, the control system 49 is configured to control the delivery of irrigation fluid from the source 21 of irrigation fluid to the irrigated catheter 15. The control system 49 can be configured to deliver irrigation fluid at a first flow rate in a first time period $T_1$ and at a second flow rate in a second time period $T_2$. The second flow rate can be at least about half of the first flow rate in accordance with an embodiment of the disclosure. The first flow rate can be approximately 7 ml/min in accordance with an embodiment of the disclosure. Although 7 ml/min is described herein, the first flow rate can be greater or lower in other embodiments of the disclosure. The second flow rate can be approximately 3.5 ml/min in accordance with an embodiment of the disclosure. Although 3.5 ml/min is described herein, the second flow rate can be greater or lower in other embodiments of the disclosure. The first time period $T_1$ can substantially coincide with the beginning of an RF ablation cycle in accordance with an embodiment of the disclosure and as generally illustrated in FIG. 14. The first time period $T_1$ can be approximately about 10-15 seconds in accordance with an embodiment of the disclosure. The second time period $T_2$ is temporally after the first time period. The second time period $T_2$ can be approximately about 75-80 seconds in accordance with an embodiment of the disclosure, such that the duration of the RF ablation cycle is about 90 seconds.

During the first time period $T_1$ having the first flow rate of irrigation fluid, the ability of the thermal sensor 28 to measure the temperature of the targeted tissue 13 can be affected and/or suppressed by the volume of irrigation fluid passing through the ablation electrode assembly 10, 110, 210, 310. Accordingly, the thermal sensor 28 can register a temperature measurement that is lower than the actual temperature of the distal end portion of the irrigated catheter 15 and/or the targeted tissue 13, causing the ECU 45 to calculate a power delivery rate value for the ablation generator 39 that is higher than would otherwise be calculated. Therefore, the first flow rate can be configured to intentionally suppress temperature feedback control and allow the electrical generator 39 to thereby practically temporarily increase power output. The ECU 45 can output the calculated power delivery rate value to the control system 39. The control system 39 is configured to receive the power delivery rate value and to control energy delivery of the ablation generator 39 based at least in part on the power delivery rate value.

Because the power delivery rate value for the ablation generator 39 is higher (based on a lower temperature measurement than would otherwise be registered by the thermal sensor 28), the control system 39 delivers power at greater levels during the first time period $T_1$. For example and without limitation, the ablation generator 39 can deliver energy at a first power level of between approximately 30 Watts to 40 Watts in accordance with an embodiment of the disclosure. In particular, the ablation generator 39 can deliver energy at a first power level of approximately 35 Watts during the first time period $T_1$. Although particular power levels for the first power level are mentioned herein, the first power level can be lower or greater in various other embodiments of the disclosure. By suppressing the temperature feedback mechanism and allowing the generator 39 to temporarily increase power output, the system 11 is essentially operating in a "power control mode." In a power control mode, a power setting is supplied by the generator 39 irrespective of temperature feedback from the thermal sensor 28 in the ablation electrode assembly 10, 110, 210, 310 of the catheter 15. One advantage of a power control mode is the ability to deliver a higher and/or substantially fixed power output, which can potentially reduce procedural variables during RF ablation and create more consistent lesions. When operating in a power control mode, the first power level should account for the potential for tissue or steam pops and/or other adverse affects associated with high temperature levels. One of ordinary skill in the art should recognize the potential for tissue or steam pops and/or other adverse affects associated with high temperature levels and should select appropriate power levels to avoid such affects. Alternatively, the ECU 45 can be appropriately programmed to ensure that the control system 49 selects appropriate power levels to avoid such effects.

During the second time period $T_2$, the ablation generator 39 can deliver energy at a second power level of approximately 10 Watts to 15 Watts, for example and without limitation. The second power level can be at least one third of the first power level in accordance with an embodiment of the disclosure. Although particular power levels for the second power level are mentioned herein, the second power level can be lower or greater in various other embodiments of the disclosure. During the second time period $T_2$, the generator 39 is operating in a "temperature control mode." In a temperature control mode, the power output by the generator 39 is reduced during the RF ablation cycle in order to maintain a desired set-point temperature. In the temperature-control mode of the second time period $T_2$, the reduced power output by the generator 39 generally trends toward a level that provides a steady state temperature at the ablation site (e.g., the interface between the distal end of the irrigated catheter 15 and the targeted tissue 13). One advantage of a temperature control mode is that a steady-state temperature at the ablation site can promote lesion growth primarily through conductive heat transfer.

Referring now to FIG. 14, a chart comparing (i) the temperature of the distal end portion of an ablation electrode assembly 10, 110, 210, 310 of an irrigated catheter 15, (ii) the temperature of targeted tissue 13, and (iii) the power delivered by an ablation generator 39 connected to the irrigated catheter 15, each over the time of an ablation cycle, for a system 11 in accordance with an embodiment of the disclosure is illustrated. FIG. 14 generally illustrates data in accordance with a power setting of 50 Watts and a temperature setting of 75° C. for the ablation system 37, and a transition of flow rate for irrigation fluid from approximately 7 ml/min to approximately 3.5 ml/min at about 15 seconds into the RF ablation cycle. As generally illustrated in FIG. 14, the temperature of the targeted tissue 13 rises approximately at least the same as the temperature of the distal end portion of the irrigated catheter 15 in connection with a system in accordance with an embodiment of the disclosure. A higher temperature of the targeted tissue 13 is achieved first compared to the temperature of the distal end portion of the irrigated catheter 15. A high peak temperature for both the targeted tissue 13 and the distal end portion of the irrigated catheter 15 is reached at about the time of the transition to a lower flow rate of irrigation fluid (or the transition from the first time period $T_1$ to the second time period $T_2$ that occurs at about 15 seconds into the RF ablation cycle). During the second time period $T_2$ of the cycle when the second flow rate of the irrigation fluid is active, the temperature of the targeted tissue 13 decreases and substantially levels out to become substantially near parallel to the indicated temperature of the distal end portion of the irrigated catheter 15 and is maintained.

The temperature of the targeted tissue 13 thus reaches an approximately steady-state condition during the second time period $T_2$. Such a steady-state condition can be especially advantageous in connection with predicting tissue temperature during clinical use of the irrigated catheter. Depending on, for example, the type of irrigated catheter 15, the location, size, and other characteristics of the targeted tissue 13, the power delivery, and the first and second flow rates of irrigation fluid, both the degree of parallelism between the measured temperature for the distal end of the irrigated catheter 15 and the measured temperature for the targeted tissue 13, as well as the temperature differential between the measured temperature for the distal end of the irrigated catheter 15 and the measured temperature for the targeted tissue 13 can vary.

Figure 15:
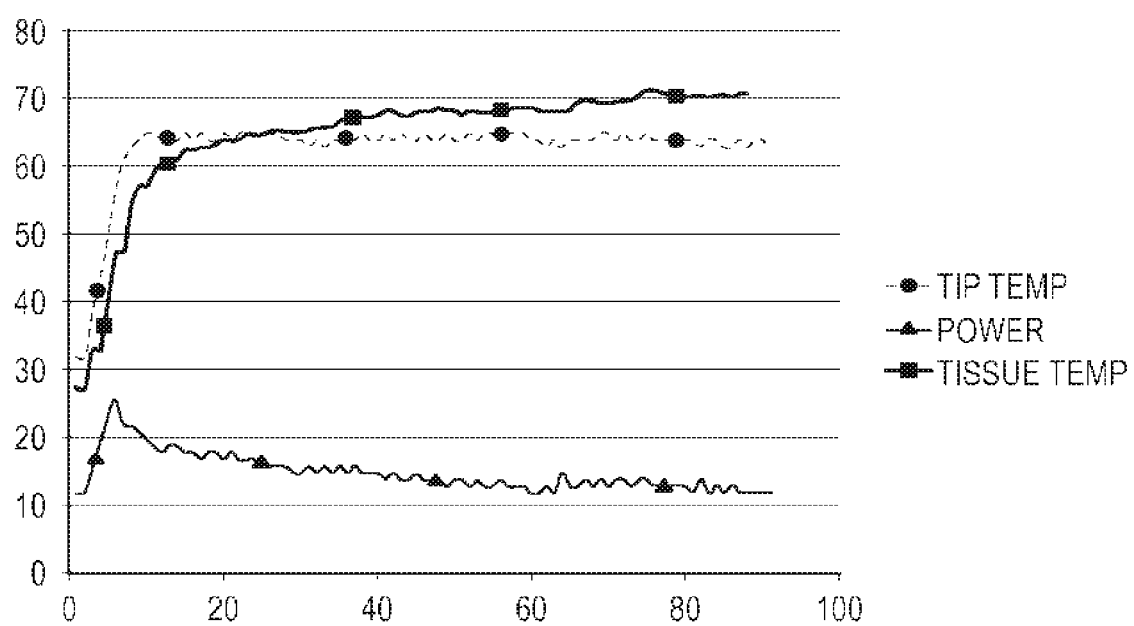
FIG. 15 is a chart comparing the temperature of the distal end portion of an ablation electrode assembly of an irrigated catheter, the temperature of targeted tissue, and power delivered by an ablation generator connected to the irrigated catheter over time in accordance with a typical irrigation flow rate sequence having a constant flow rate of irrigation fluid.

In contrast, FIG. 15 is a first comparative chart generally illustrating (i) the temperature of the distal end portion of an ablation electrode assembly of the same irrigated catheter as was used to generate the data in FIG. 14, (ii) the temperature of targeted tissue, and (iii) the power delivered by an ablation generator connected to the irrigated catheter, each over time in accordance with a typical irrigation flow rate sequence having a constant flow rate of irrigation fluid. FIG. 15 generally illustrates data in accordance with a power setting of 50 Watts and a temperature setting of 65° C. for the ablation system 37. The flow rate of irrigation fluid is approximately 7 ml/min, which is considered to be in the high-flow regime. As generally illustrated in FIG. 15, the temperature of the targeted tissue rises more slowly than the temperature of the distal end portion of the irrigated catheter in connection with a system utilizing a typical irrigation flow rate sequence having a constant flow rate of irrigation fluid. A higher temperature of the distal end portion of the irrigated catheter is achieved first as compared to the temperature of the targeted tissue. While the temperature measurement for the distal end portion of the irrigated catheter substantially levels out and is maintained, the temperature of the targeted tissue continues to rise beyond the temperature measurement for the distal end portion of the irrigated catheter as power is delivered. Accordingly, during the RF ablation cycle, the temperature of the targeted tissue becomes increasingly different from the temperature measurement for the distal end portion of the irrigated catheter, thereby resulting in a decreased correlation between the temperature measurements of the irrigated catheter and the targeted tissue, especially toward the end of the RF ablation cycle.

Figure 16:
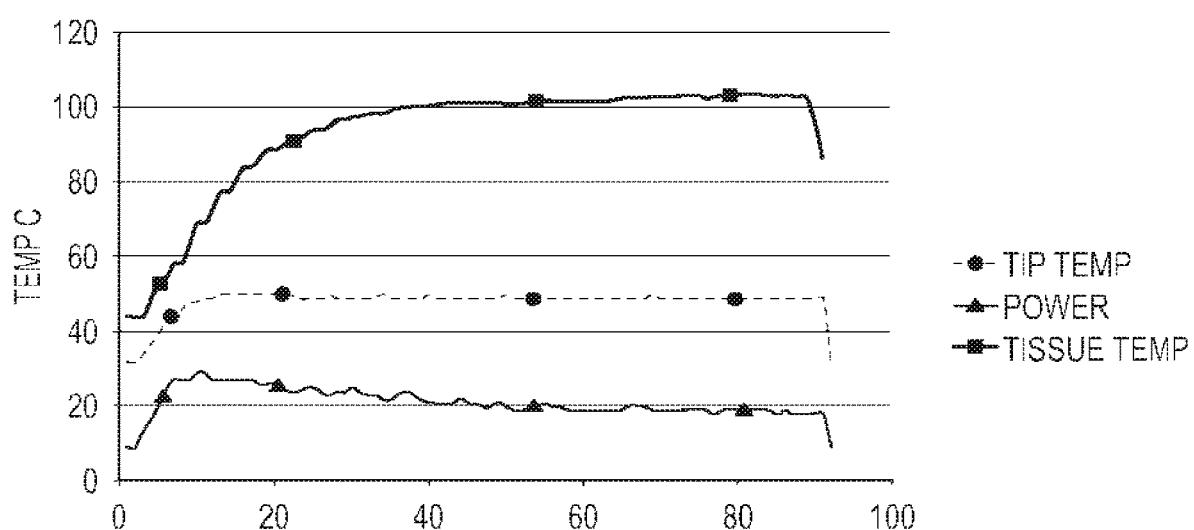
FIG. 16 is a chart comparing the temperature of the distal end portion of an ablation electrode assembly of an irrigated catheter, the temperature of targeted tissue, and power delivered by an ablation generator connected to the irrigated catheter over time in accordance with an irrigation flow rate sequence having a constant flow rate of irrigation fluid.

Referring now to FIG. 16, a second comparative chart generally illustrates (i) the temperature of the distal end portion of an ablation electrode assembly of a different irrigated catheter as was used to generate the data in FIGS. 14-15, (ii) the temperature of targeted tissue, and (iii) power delivered by an ablation generator connected to the irrigated catheter, each over time in accordance with an irrigation flow rate sequence having a constant flow rate of irrigation fluid. FIG. 16 generally illustrates data in accordance with a power setting of 30 Watts and a temperature setting of 50° C. for the ablation system 37. The flow rate of irrigation fluid is again approximately 7 ml/min, which is considered to be in the high flow regime. The irrigated catheter used to generate the data in FIG. 16 comprises an irrigated catheter generally sold under the brand name THERAPY™ COOL-PATH™ and that is commercially available from St. Jude Medical, Atrial Fibrillation Division, Inc. As generally illustrated in FIG. 16, the temperature of the targeted tissue rises significantly faster as compared to the temperature measurement of the distal end portion of the irrigated catheter. A higher temperature of the targeted tissue is achieved first and maintained as compared to the temperature of the distal end portion of the irrigated catheter. Although the temperature of the targeted tissue shows less variability over the duration of the ablation cycle, the temperature of the targeted tissue does continue to rise slightly as power is delivered. The temperature of the targeted tissue continues to climb during power delivery. The temperature measurement for the distal end portion of the irrigated catheter substantially levels out and is maintained. Accordingly, there can still be a slightly decreased correlation between the temperature measurements of the irrigated catheter and the targeted tissue over the duration of the RF ablation cycle.

In accordance with an embodiment of the system utilizing a first flow rate of irrigation fluid that is higher and a second flow rate of irrigation fluid that is lower, the particular flow rate of the irrigation fluid can be modified based on information and feedback received during the RF ablation cycle. For example and without limitation, the feedback can relate to time, temperature, and/or impedance. For example, the first flow rate can be based at least in part on temperature measurements taken by the thermal sensor 28. If temperature measurements from thermal sensors 28 meet a certain, predefined threshold, a higher first flow rate can be desirable. If temperature measurements from thermal sensors 28 go below a certain, predefined threshold, a lower first flow rate can be desirable. For another example, the second flow rate can also be based at least in part on temperature measurements taken by the thermal sensor 28. If temperature measurements from thermal sensors 28 meet a certain, predefined threshold, a higher second flow rate can be desirable. If temperature measurements from thermal sensors 28 go below a certain, predefined threshold, a lower second flow rate can be desirable. The thermal sensors 28 can thus provide feedback which can be implemented in a control algorithm executed by the ECU 45 and/or the control system 49 of the system 11 to automatically control the flow rates of irrigation fluid within irrigated catheter 15 in accordance with an embodiment of the disclosure. The ECU 45 and/or the control system 49 can be configured to ensure that the first flow rate be at least two times the second flow rate, regardless of the feedback control mechanism.

In accordance with those embodiments of the disclosure wherein the irrigation fluid is preheated to biological temperature, the tissue temperature feedback during an ablation procedure can be improved. In particular, if the irrigation fluid is at or around about 37° C., for example, when it is utilized in an ablation electrode assembly 10, 110, 210, 310, then the temperature measurement taken by the thermal sensor 28 will be attributable to ohmic heating (or Joule heating) of the targeted tissue 13 and will not be significantly affected by loss of energy that is converted to heat in connection with raising the temperature of the irrigation fluid. Accordingly, the temperature measurement taken by the thermal sensor 28 will have an improved correlation to total energy supplied during an RF ablation cycle. Accordingly, there will be an improved correlation between the temperature of the distal end portion of ablation electrode assemblies 10, 110, 210, 310 and the temperature of the targeted tissue 13 since the energy lost to convection will be reduced, thereby improving lesion development and procedure outcomes.

In accordance with some embodiments of the invention, the temperature of the irrigation fluid can be modified based on information and feedback received during the RF ablation cycle. For example and without limitation, the feedback can relate to temperature measurements taken by the thermal sensor 28. For example, it can be desirable in accordance with an embodiment of the disclosure for the temperature of the irrigation fluid to be modified so as to be based on and/or correspond to the temperature measurements taken by the thermal sensor 28. The thermal sensors 28 can thus provide feedback which can be implemented in a control algorithm executed by the ECU 45 and/or the control system 49 of the system 11 to automatically control the temperature of irrigation fluid within irrigated catheter 15 in accordance with an embodiment of the disclosure. By modifying the temperature of the irrigation fluid so as to correspond to the temperature measurements taken by the thermal sensor 28, the temperature measurement taken by the thermal sensor 28 will be attributable to ohmic heating of the tissue (and there will be a reduction in energy lost to convection), thereby causing the temperature of the distal end portion of the ablation electrode assemblies 10, 110, 210, 310 and the targeted tissue 13 to more closely correspond and have a reduced temperature differential. Improved correlation between the temperature of the distal end portion of the ablation electrode assemblies 10, 110, 210, 310 and the targeted tissue can allow for improved procedure control, improved lesion formation, and a lower incidence of tissue pops or char.

The first and second flow rates can be based on feedback other than temperature feedback. For example and without limitation, in other embodiments of the disclosure, the first and second flow rates can be based at least in part on an impedance measurement taken by one or more positioning electrode as described hereinabove. In particular, the positioning electrodes can be used to sense an impedance at a particular location and transmit a representative signal to the ECU 45 (or other external computer or processor). In other embodiments, the cycle times for the RF ablation cycles can be based on feedback relating to temperature, time, impedance, and/or electrogram information. Circuitry for implementing the feedback automatically in a control algorithm can be readily provided by those having ordinary skill in the art after becoming familiar with the teachings herein.

Valve members, for example and without limitation, such as those shown and described in co-owned U.S. Patent Application Publication No. 2008/0161795 titled "Irrigated Ablation Catheter System With Pulsatile Flow To Prevent Thrombus," the entire disclosure of which is incorporated herein by reference, or other similar flow control features can be used in connection with irrigated catheter 15 in order to alternate between the first and second flow rate. In other embodiments, the flow control features can be part of an ancillary control system separate from and to be used in conjunction with the irrigated catheter 15.

Figure 17:
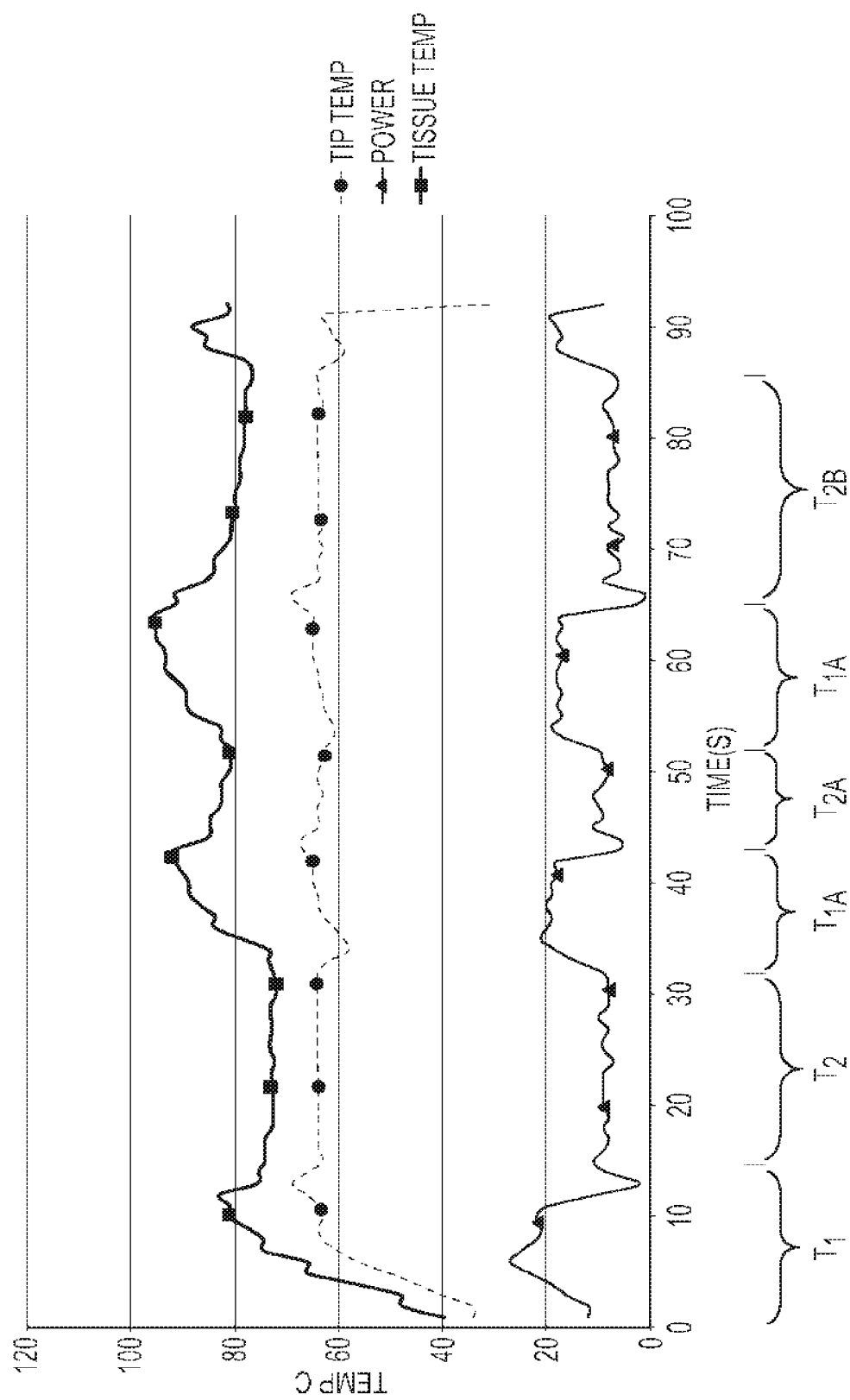
FIG. 17 is a chart comparing the temperature of the distal end portion of an ablation electrode assembly of an irrigated catheter, the temperature of the targeted tissue, and power deliver by an ablation generator connected to the irrigated catheter over time in accordance with an embodiment of the disclosure.

Referring now to FIG. 17, a chart comparing (i) the temperature of the distal end portion of an ablation electrode assembly 10, 110, 210, 310 of an irrigated catheter 15, (ii) the temperature of targeted tissue 13, and (iii) the power delivered by an ablation generator 39 connected to the irrigated catheter 15, each over the time of an ablation cycle, for a system 11 in accordance with another embodiment of the disclosure is illustrated. FIG. 17 generally illustrates data in accordance with a power setting of 50 Watts and a temperature setting of 65° C. for the ablation system 37. In accordance with this embodiment of the disclosure, the control system 49 can be configured to deliver irrigation fluid at a first flow rate (e.g., about 7 ml/min, about 5 ml/min, about 3 ml/min, etc.) in a first time period $T_1$ and at a second flow rate (e.g., about 3.5 ml/min, about 2.5 ml/min, about 1.5 ml/min, etc.) in a second time period $T_2$. The first time period $T_1$ can coincide with the beginning of an RF ablation cycle in accordance with an embodiment of the disclosure and as generally illustrated in FIG. 17. The first time period $T_1$ can be approximately about 15 seconds in accordance with an embodiment of the disclosure. The second time period $T_2$ is temporally after the first time period. The second time period $T_2$ can be approximately about 20 seconds in accordance with an embodiment of the disclosure.

Following the second time period $T_2$, the flow rate of irrigation fluid can alternate between the first flow rate (e.g., about 7 ml/min, about 5 ml/min, about 3 ml/min, etc.) and the second flow rate (e.g., about 3.5 ml/min, about 2.5 ml/min, about 1.5 ml/min) in alternating time periods $T_{1A}$, $T_{1B}$ and $T_{2A}$, $T_{2B}$, respectively. As generally illustrated in FIG. 17, the temperature of the targeted tissue 13 rises approximately at least the same, or greater than, the temperature of the distal end portion of the irrigated catheter 15 in accordance with an embodiment of the disclosure. A higher temperature of the targeted tissue 13 is achieved first compared to the temperature of the distal end portion of the irrigated catheter 15. A high peak temperature for both the targeted tissue 13 and the distal end portion of the irrigated catheter 15 is reached at about the time of the transition to a lower flow rate of irrigation fluid (or the transition from the first time period $T_1$ to the second time period $T_2$ that occurs at about 15 seconds into the RF ablation cycle). During the second time period $T_2$ of the cycle when the second flow rate of the irrigation fluid is active, the temperature of the targeted tissue 13 decreases and substantially levels out to become substantially near parallel to the indicated temperature of the distal end portion of the irrigated catheter 15 and is maintained.

During time periods $T_1$, $T_{1A}$, and $T_{1B}$ having the first flow rate, the power delivery from generator 39 is increased (e.g., due to the suppression of temperature feedback control by the increased flow rate of irrigation fluid), and there may be a corresponding spike in both temperature of the distal end portion of the irrigated catheter 15 and temperature of the targeted tissue 13. During time periods $T_2$, $T_{2A}$, and $T_{2B}$ having the second flow rate, the temperature of the targeted tissue 13 and the indicated temperature of the distal end portion of the irrigated catheter 15 are substantially near parallel. The benefit of alternating the first and second flow rates in alternating time periods after an initial first (e.g., high) flow rate in time period $T_1$ and an initial second (e.g., low) flow rate in time period $T_2$ is that the overall energy delivery during the RF ablation cycle is increased, while still helping to ensure that the temperature of the targeted tissue 13 remains below a predetermined threshold that is considered medically safe. For example and without limitation, the predetermined threshold can be about 100° C. Although about 100° C. is mentioned herein as a predetermined threshold, the predetermined threshold may be higher or lower in other embodiments of the disclosure.

Figure 18:
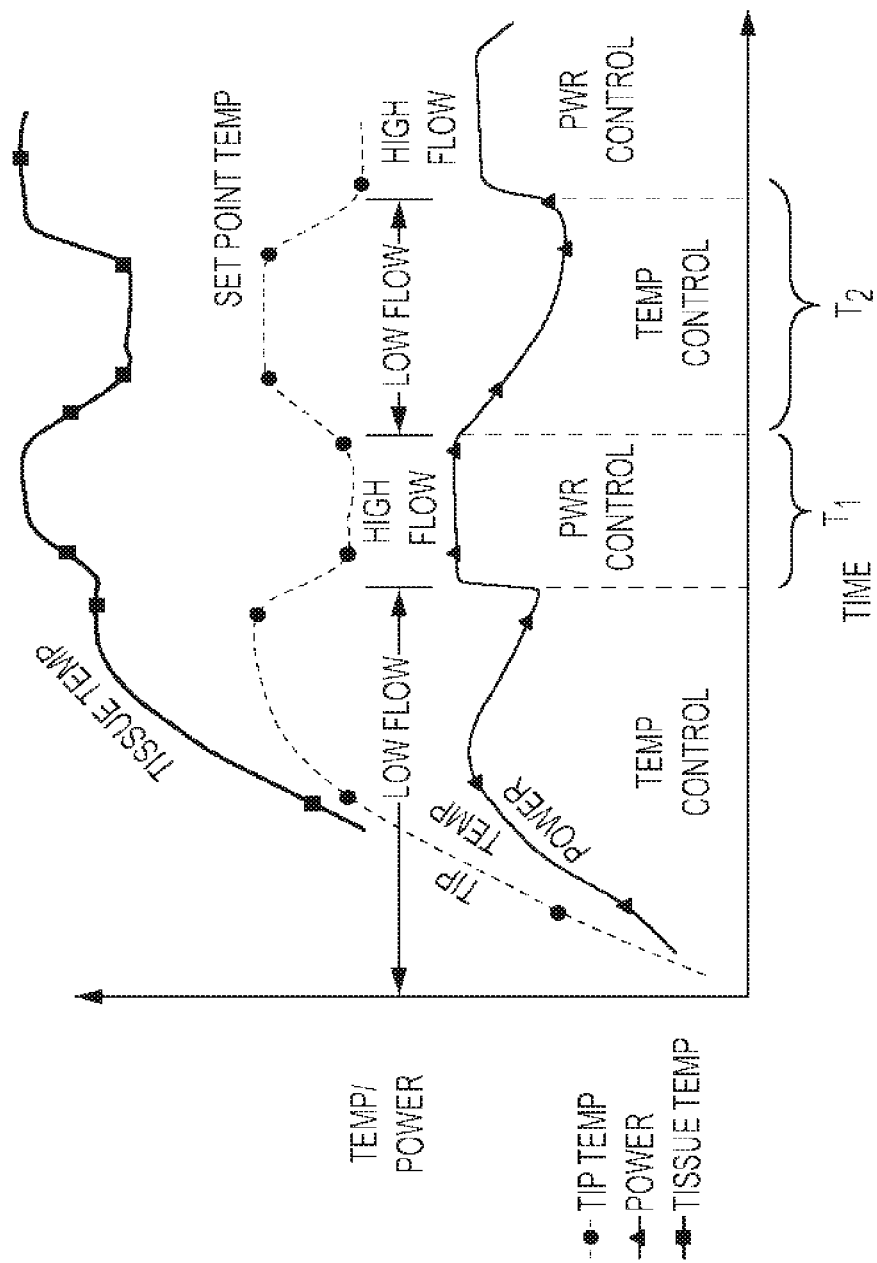
FIG. 18 is a chart comparing the temperature of the distal end portion of an ablation electrode assembly of a catheter, the temperature of the targeted tissue, and power delivered by an ablation generator connected to the catheter of over time in accordance with another embodiment of the disclosure.

In accordance with another embodiment of the disclosure, the first time period $T_1$ does not coincide with the beginning of an ablation cycle. Rather, the first time period $T_1$ occurs in the middle of an ablation cycle. During the first time period $T_1$, the system 11 operates in a power control mode in which a substantially constant and/or fixed power setting is supplied by the generator 39 irrespective of temperature feedback from the thermal sensor 28 in the ablation electrode assembly 10, 110, 210, 310 of the catheter 15. Accordingly, in this embodiment, the first power level is substantially constant over the duration of the first time period $T_1$. FIG. 18 generally illustrates (i) the temperature of the distal end portion of an ablation electrode assembly of a catheter 15, (ii) the temperature of the targeted tissue 13, and (iii) power delivered by an ablation generator 39 connected to the catheter 15, each over time in accordance with another embodiment of the disclosure. FIG. 18 generally illustrates that the power level is substantially constant during the first time period $T_1$. The power control mode during the first time period $T_1$ can also correspond with a higher flow rate of irrigation fluid. During a second time period $T_2$ that is temporally after the first time period $T_1$, the ablation generator 39 operates in a temperature control mode in which the ablation generator 39 provides a reduced power output that is configured to maintain a desired set point temperature. The temperature control mode during the second time period $T_2$ can also correspond with a lower flow rate of irrigation fluid.

Although system 11 is described as utilizing an irrigated catheter that is configured to deliver a first flow rate of irrigation fluid in a first time period $T_1$ and a second flow rate of irrigation fluid in a second time period $T_2$, the system 11 does not necessarily require the delivery of irrigation fluid in order to provide advantages during an RF ablation cycle in a clinical setting. In particular, an increased power delivery level in a first time period $T_1$ (e.g., such as the increased power delivery level made possible by the high flow rate of irrigation fluid) and a decreased power delivery level in a second time period $T_2$ (e.g., such as the decreased power delivery level based on temperature feedback) can itself provide advantages during an RF ablation cycle even in the absence of irrigation fluid delivery. Although the delivery of irrigation fluid is not necessarily required, the delivery of irrigation fluid during the delivery of energy at a first (e.g., increased) power level is preferred because the irrigation fluid provides for tissue surface cooling of the targeted tissue 13 and coagulum management during the RF ablation cycle.

Figure 19:
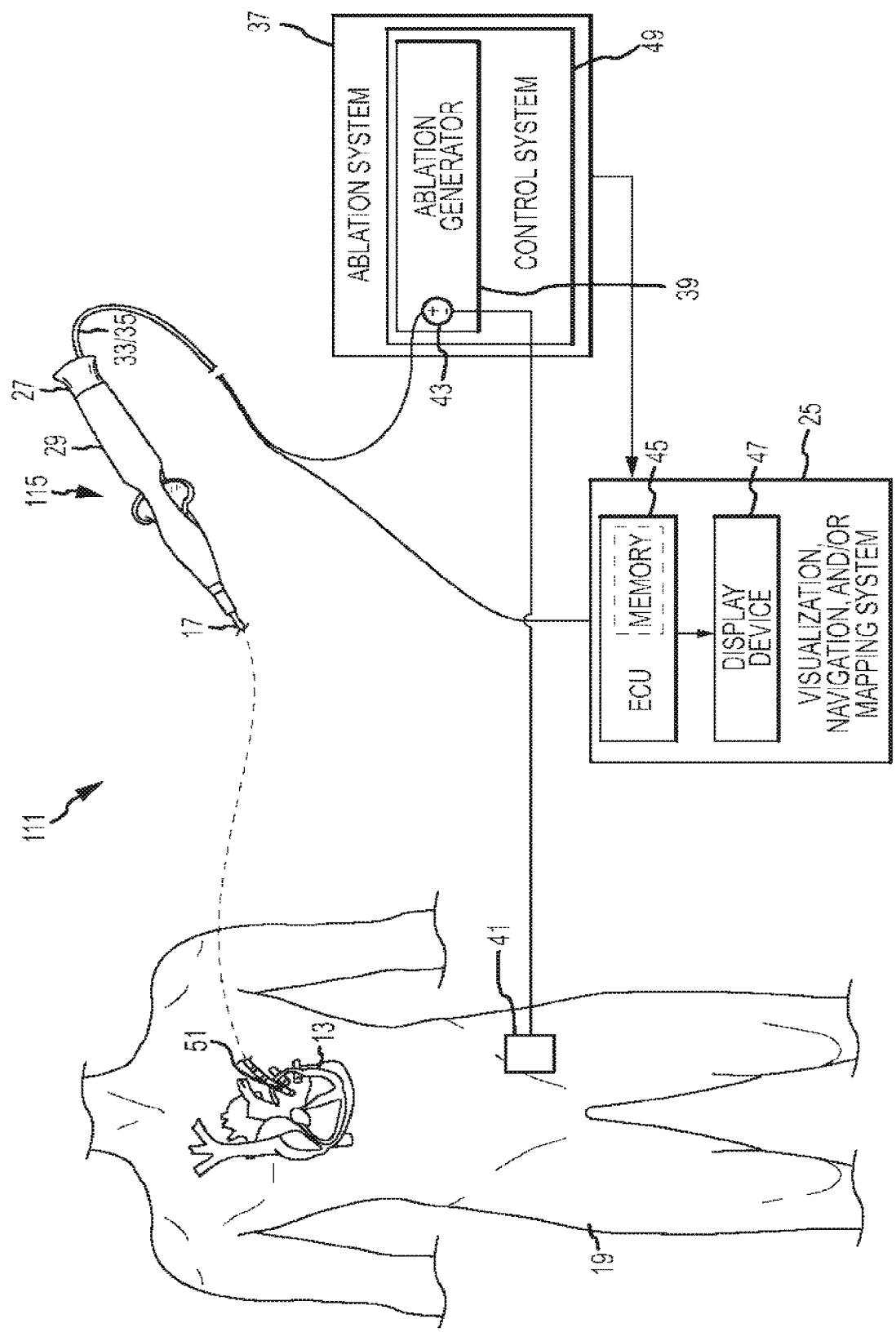
FIG. 19 is a diagrammatic view of another system for performing one more diagnostic and/or therapeutic functions in association with cardiac tissue.

Referring now to FIG. 19, in embodiments of the disclosure that do not utilize the delivery of irrigation fluid, the system 111 is identical to the system 11, except that the catheter 115 does not necessarily comprise an irrigated catheter and does not necessarily require a source 21 of irrigation fluid. The catheter 115 comprises a non-irrigated catheter in an embodiment of the disclosure. The catheter 115 can comprise an irrigated catheter in other embodiments of the disclosure, although the delivery of irrigation fluid is not necessarily required. The system 111 further comprises ablation generator 39 that is identical to the ablation generator described hereinabove. The ablation generator 39 is configured to deliver energy to at least a portion of the catheter 115. The system 111 further comprises a control system 49 that is identical to the control system described hereinabove. The control system is configured to control energy delivery of the ablation generator 39.

The control system 49 is configured to deliver energy at a first power level in a first time period $T_1$ and at a second power level in a second time period $T_2$. The first power level can comprise between approximately 30 Watts to 40 Watts in accordance with an embodiment of the disclosure. In particular, the first power level can comprise approximately 35 Watts in accordance with an embodiment of the disclosure. The first time period $T_1$ is between about 10 seconds and about 15 seconds. The second time period $T_2$ is temporally after the first time period $T_1$. The second power level is at least one third of the first power level in accordance with an embodiment of the disclosure. The second power level can comprise between approximately 10 Watts to 15 Watts in accordance with an embodiment of the disclosure. Although particular power levels for the first and second power levels are mentioned herein, the first and/or second power levels can be lower or greater in various other embodiments of the disclosure. The control system 49 is configured to control energy delivery of the ablation generator 39 in accordance with one or more user specified control parameters (e.g., power). In addition or alternatively, the control system 49 is configured to control energy delivery of the ablation generator 39 through various feedback sensing and control circuitry. Circuitry for implementing the feedback automatically in a control algorithm can be readily provided by those having ordinary skill in the art after becoming familiar with the teachings herein.

Although at least four embodiments of this disclosure and at least four methods of use therefor have been described above with a certain degree of particularity, those skilled in the art could make numerous alterations to the disclosed embodiments without departing from the spirit or scope of this disclosure. For example, additional thermal sensors can be connected to the ablation electrode assemblies (e.g., external to the outer shell) for additional temperature measurements. For another example, although the ablation electrode assemblies include an irrigation port as described and illustrated and although exemplary methods of using ablation electrode assemblies to provide irrigation fluid have been described and illustrated, the ablation electrode assemblies could be used and provide benefits even if irrigation fluid is not utilized in the ablation electrode assemblies. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

What is claimed is:

1. A method of delivering fluid to an irrigated catheter including an ablation electrode assembly, comprising:
   delivering a pulsatile flow of irrigation fluid within at least a portion of the irrigated catheter;
   wherein the irrigation fluid has a first flow rate in a first time period and the irrigation fluid has a second flow rate in a second time period,
   wherein the first flow rate and the second flow rate are different,
   wherein the first flow rate and the second flow rate are based at least in part on a plurality of temperature measurements taken by thermal sensors disposed within the irrigated catheter, wherein the thermal sensors include at least two thermal sensors positioned to take temperature measurements of the irrigation fluid as the irrigation fluid flows in a direction to exit the irrigated catheter through the ablation electrode assembly, and wherein the first flow rate and the second flow rate alternate and recur at intervals over time.

2. The method of claim 1, wherein the first flow rate and the second flow rate are based in part on temperature measurements taken by thermal sensors disposed within the irrigated catheter and in part on impedance measurements taken by positioning electrodes located on the irrigated catheter.

3. The method of claim 1, wherein the first flow rate is higher than the second flow rate.

4. The method of claim 3, wherein the second flow rate is at least about half of the first flow rate.

5. The method of claim 1, wherein the first time period is about 10-15 seconds and the second time period is about 75-80 seconds.

6. The method of claim 1, further comprising:
delivering ablation energy from the electrode assembly connected to the irrigated catheter;
wherein the ablation energy has a first power level during the first time period and the ablation energy has a second power level during the second time period.

7. The method of claim 6, wherein the first power level is higher than the second power level.

8. The method of claim 7, wherein the second power level is at least about one third of the first power level.

9. The method of claim 1, wherein delivering the pulsatile flow of irrigation fluid further comprises directing the irrigation fluid within at least a portion of at least one of an inner core member, an outer shell, and an annular space between the inner core member and the outer shell, the annular space radially surrounding the inner core member.

10. The method of claim 9, wherein the inner core member comprises a first radially extending passageway that extends from an inner chamber through an outer surface of the inner core member, wherein the first radially extending passageway is in fluid communication with the annular space.

11. The method of claim 1, wherein the first time period and the second time period are based at least in part on the temperature measurements taken by the thermal sensors disposed within the irrigated catheter.

12. A method of delivering fluid and energy to an irrigated catheter including an ablation electrode assembly, comprising:
delivering a pulsatile flow of irrigation fluid within at least a portion of the irrigated catheter; and
delivering ablation energy from connected to the irrigated catheter;

wherein the irrigation fluid has a first flow rate in a first time period and the irrigation fluid has a second flow rate in a second time period, wherein the first flow rate and the second flow rate are different, and wherein the first flow rate and the second flow rate are based at least in part on a plurality of temperature measurements taken by thermal sensors disposed within the irrigated catheter, wherein the thermal sensors include at least two thermal sensors positioned to take temperature measurements of the irrigation fluid as the irrigation fluid flows in a direction to exit the irrigated catheter through the ablation electrode assembly;

wherein the ablation energy has a first power level during the first time period and the ablation energy has a second power level during the second time period, wherein the first power level and the second power level are different, and wherein the first time period and the second time period alternate and recur at intervals over time.

13. The method of claim 12, wherein the first flow rate and the second flow rate are based in part on the temperature measurements taken by the thermal sensors disposed within the irrigated catheter and in part on impedance measurements taken by positioning electrodes located on the irrigated catheter.

14. The method of claim 12, wherein the first flow rate is higher than the second flow rate, and wherein the first power level is higher than the second power level.

15. The method of claim 14, wherein the second flow rate is at least about half of the first flow rate, and wherein the second power level is at least about one third of the first power level.

16. The method of claim 12, wherein the first time period is about 10-15 seconds and the second time period is about 75-80 seconds.

17. The method of claim 12, wherein delivering the pulsatile flow of irrigation fluid further comprises directing the irrigation fluid within at least a portion of at least one of an inner core member, an outer shell, and an annular space between the inner core member and the outer shell, the annular space radially surrounding the inner core member.

18. The method of claim 17, wherein the inner core member comprises a first radially extending passageway that extends from an inner chamber through an outer surface of the inner core member, wherein the first radially extending passageway is in fluid communication with the annular space.

19. The method of claim 12, wherein the first time period and the second time period are based at least in part on the temperature measurements taken by the thermal sensors disposed within the irrigated catheter.

* * * * *